(12) United States Patent
Hollis et al.

(10) Patent No.: US 10,799,250 B2
(45) Date of Patent: Oct. 13, 2020

(54) PLANTAR PLATE REPAIR

(71) Applicant: CROSSROADS EXTREMITY SYSTEMS, LLC, Memphis, TN (US)

(72) Inventors: M. Chad Hollis, Collierville, TN (US); Chad Webster, Memphis, TN (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 159 days.

(21) Appl. No.: 16/193,633

(22) Filed: Nov. 16, 2018

(65) Prior Publication Data

US 2019/0083114 A1 Mar. 21, 2019

Related U.S. Application Data

(63) Continuation of application No. 15/018,832, filed on Feb. 8, 2016, now Pat. No. 10,130,377.

(51) Int. Cl.
| | |
|---|---|
| *A61B 17/16* | (2006.01) |
| *A61B 17/04* | (2006.01) |
| *A61B 17/84* | (2006.01) |
| *A61B 17/88* | (2006.01) |
| *A61B 50/33* | (2016.01) |
| *A61B 17/02* | (2006.01) |
| *A61B 17/06* | (2006.01) |
| *A61B 17/68* | (2006.01) |

(52) U.S. Cl.
CPC ........ *A61B 17/1682* (2013.01); *A61B 17/025* (2013.01); *A61B 17/0401* (2013.01); *A61B 17/0483* (2013.01); *A61B 17/06066* (2013.01); *A61B 17/683* (2013.01); *A61B 17/848* (2013.01); *A61B 17/8861* (2013.01); *A61B 17/8866* (2013.01); *A61B 50/33* (2016.02); *A61B 17/0485* (2013.01); *A61B 17/842* (2013.01); *A61B 2017/0409* (2013.01); *A61B 2017/0414* (2013.01); *A61B 2017/0445* (2013.01); *A61B 2017/0458* (2013.01); *A61B 2017/0479* (2013.01); *A61B 2017/06023* (2013.01); *A61B 2017/681* (2013.01)

(58) Field of Classification Search
CPC .................. A61B 17/0401; A61B 17/1682
See application file for complete search history.

(56) References Cited

U.S. PATENT DOCUMENTS

| | | | |
|---|---|---|---|
| 373,372 | A | 11/1887 | King |
| 722,105 | A | 3/1903 | Hervey |
| 2,370,545 | A | 2/1945 | Karle |
| 3,206,018 | A | 9/1965 | Lewis |
| 3,845,772 | A | 11/1974 | Smith |
| 5,100,418 | A | 3/1992 | Yoon |

(Continued)

FOREIGN PATENT DOCUMENTS

| | | |
|---|---|---|
| AU | 2012282919 | 1/2014 |
| AU | 2014212830 | 3/2015 |

(Continued)

*Primary Examiner* — Christian A Sevilla
(74) *Attorney, Agent, or Firm* — Maywood IP Law; G. Jo Hays; Davis W. Meibos

(57) ABSTRACT

A kit for plantar plate repair may include implants and instruments specific to the procedure, such as an implant assembly, a needle assembly, a distractor, a needle driver, and k-wires. Methods of assembling the items of the kit and methods of plantar plate repair are disclosed.

5 Claims, 31 Drawing Sheets

(56) References Cited

U.S. PATENT DOCUMENTS

| | | | |
|---|---|---|---|
| 5,171,250 A | 12/1992 | Yoon | |
| 5,366,459 A | 11/1994 | Yoon | |
| 5,437,680 A | 8/1995 | Yoon | |
| 5,445,167 A | 8/1995 | Yoon | |
| 5,478,353 A | 12/1995 | Yoon | |
| 5,480,405 A | 1/1996 | Yoon | |
| 5,542,949 A | 8/1996 | Yoon | |
| 5,584,836 A | 12/1996 | Ballintyn | |
| 5,899,938 A | 5/1999 | Sklar | |
| 5,941,882 A | 8/1999 | Jammet | |
| 6,110,207 A | 8/2000 | Eichhorn | |
| 6,533,816 B2 | 3/2003 | Sklar | |
| 6,554,862 B2 | 4/2003 | Hays | |
| 6,562,043 B1 | 5/2003 | Chan | |
| 6,626,910 B1 | 9/2003 | Hugues | |
| 6,660,009 B1 | 12/2003 | Azar | |
| 6,902,573 B2 | 6/2005 | Strobel | |
| 6,932,841 B2 | 8/2005 | Sklar | |
| 6,939,379 B2 | 9/2005 | Sklar | |
| 7,083,647 B1 | 8/2006 | Sklar | |
| 7,204,802 B2 | 4/2007 | De Leval | |
| 7,329,281 B2 | 2/2008 | Hays | |
| 7,485,136 B2 | 2/2009 | Chan | |
| 7,569,059 B2 | 8/2009 | Cerundolo | |
| 7,578,844 B2 | 8/2009 | Sklar | |
| 7,588,587 B2 | 9/2009 | Barbieri | |
| 7,611,454 B2 | 11/2009 | De Leval | |
| 7,837,731 B2 | 11/2010 | Sklar | |
| 7,938,847 B2 | 5/2011 | Fanton | |
| 8,048,158 B2 | 11/2011 | Hays | |
| 8,100,968 B2 | 1/2012 | Chan | |
| 8,277,484 B2 | 10/2012 | Barbieri | |
| 8,298,285 B2 | 10/2012 | Sklar | |
| 8,480,689 B2 | 7/2013 | Spivey | |
| 8,529,589 B2 | 9/2013 | Cartledge | |
| 8,562,680 B2 | 10/2013 | Hays | |
| 8,636,799 B2 | 1/2014 | Sklar | |
| 8,641,597 B2 | 2/2014 | De Leval | |
| 8,696,716 B2 | 4/2014 | Kartalian | |
| 8,721,650 B2 | 5/2014 | Fanton | |
| 8,778,023 B2 | 7/2014 | Sklar | |
| 8,784,427 B2 | 7/2014 | Fallin | |
| 8,801,727 B2 | 8/2014 | Chan | |
| 8,882,816 B2 | 11/2014 | Kartalian | |
| 8,882,834 B2 | 11/2014 | Sinnott | |
| 8,888,849 B2 | 11/2014 | Fallin | |
| 8,900,269 B2 | 12/2014 | Takahashi | |
| 8,951,263 B2 | 2/2015 | Sinnott | |
| 9,101,399 B2 | 8/2015 | Kartalian | |
| 10,130,377 B2 | 11/2018 | Hollis | |
| 2001/0047206 A1 | 11/2001 | Sklar | |
| 2002/0055744 A1* | 5/2002 | Reiley | A61B 17/15 606/79 |
| 2005/0245932 A1 | 11/2005 | Fanton | |
| 2006/0282081 A1 | 12/2006 | Fanton | |
| 2006/0282082 A1 | 12/2006 | Fanton | |
| 2006/0282083 A1 | 12/2006 | Fanton | |
| 2007/0156149 A1 | 7/2007 | Fanton | |
| 2007/0156150 A1 | 7/2007 | Fanton | |
| 2007/0156176 A1 | 7/2007 | Fanton | |
| 2007/0255317 A1 | 11/2007 | Fanton | |
| 2008/0177302 A1* | 7/2008 | Shurnas | A61B 17/683 606/228 |
| 2008/0319459 A1 | 12/2008 | Al-najjar | |
| 2011/0009867 A1 | 1/2011 | Oren | |
| 2011/0238113 A1 | 9/2011 | Fanton | |
| 2011/0301648 A1* | 12/2011 | Lofthouse | A61B 17/0401 606/300 |
| 2012/0265301 A1* | 10/2012 | Demers | A61B 17/8061 623/16.11 |
| 2013/0012949 A1 | 1/2013 | Fallin | |
| 2013/0012965 A1 | 1/2013 | Sinnott | |
| 2013/0023929 A1 | 1/2013 | Sullivan | |
| 2013/0023988 A1 | 1/2013 | Sinnott | |
| 2013/0041466 A1 | 2/2013 | Fallin | |
| 2013/0046335 A1 | 2/2013 | Deutsch | |
| 2013/0158570 A1 | 6/2013 | Sinnott | |
| 2013/0184818 A1 | 7/2013 | Coughlin | |
| 2013/0226203 A1 | 8/2013 | Sklar | |
| 2013/0245701 A1 | 9/2013 | Kartalian | |
| 2014/0094911 A1 | 4/2014 | Fallin | |
| 2014/0142697 A1 | 5/2014 | Sklar | |
| 2014/0188139 A1 | 7/2014 | Fallin | |
| 2014/0214087 A1 | 7/2014 | Wahl | |
| 2014/0296911 A1 | 10/2014 | Fanton | |
| 2015/0012093 A1 | 1/2015 | Sklar | |
| 2015/0066059 A1 | 3/2015 | Sinnott | |
| 2015/0073441 A1 | 3/2015 | Fallin | |
| 2017/0215896 A1* | 8/2017 | Stemniski | A61B 17/1739 |
| 2017/0252031 A1* | 9/2017 | Harari | A61F 2/0811 |

FOREIGN PATENT DOCUMENTS

| | | |
|---|---|---|
| AU | 2016392215 | 9/2018 |
| CA | 2732793 | 2/2009 |
| CA | 2840400 | 1/2013 |
| CA | 2883657 | 8/2014 |
| EP | 2200540 | 6/2010 |
| EP | 1917917 | 11/2011 |
| EP | 2729080 | 5/2014 |
| EP | 2879604 | 6/2015 |
| EP | 1584297 | 11/2015 |
| EP | 3413804 | 12/2018 |
| WO | WO2006115782 | 11/2006 |
| WO | WO2007073343 | 6/2007 |
| WO | WO2009018527 | 2/2009 |
| WO | WO2013009574 | 1/2013 |
| WO | WO2014120448 | 8/2014 |
| WO | WO2017138917 | 8/2017 |

* cited by examiner

PLANTAR PLATE REPAIR

CROSS-REFERENCE TO RELATED APPLICATIONS

The present application is a continuation of U.S. patent application Ser. No. 15/018,832, entitled PLANTAR PLATE REPAIR, filed on Feb. 8, 2016.

The foregoing is incorporated by reference as though set forth herein in its entirety.

TECHNICAL FIELD

The present disclosure relates to plantar plate repair in the foot. While the present disclosure is made in the context of plantar plate repair of the second metatarsophalangeal joint (MTP joint), plantar plate repair of any metatarsophalangeal joint is contemplated. Furthermore, the technology disclosed herein may be adapted without undue experimentation to palmar plate repair in the hand. The palmar plate is an analogous structure to the plantar plate. A palmar plate is associated with each metacarpophalangeal joint (MCP joint) and each interphalangeal joint in the hand.

BACKGROUND

The plantar plate is a thick ligamentous structure on the bottom of the foot under a MTP joint. The plantar plate attaches to a metatarsal and a corresponding proximal phalanx. The plantar plate cushions the bottom of the MTP joint and the distal head of the metatarsal while standing, walking, running, and the like. The plantar plate helps bring the toe to the floor while standing.

The plantar plate may become torn or otherwise compromised due to biomechanical abnormalities and/or imbalances in the foot which cause overload of one of the metatarsals and/or MTP joints. Examples of biomechanical abnormalities and/or imbalances include a long first metatarsal, a short second metatarsal, a short third metatarsal, an untreated metatarsus adductus deformity (pigeon toe deformity), arthritis of the great toe (first metatarsal, first proximal phalanx, first distal phalanx), and prior cortisone injection into a plantar plate.

A torn plantar plate causes persistent ball of foot pain despite shoe and/or activity changes, and/or changes in the position of the affected toe and/or adjacent toe(s) such as elevation of the toe (hammertoe).

Current systems for plantar plate repair tend to be bulky and/or complex. Current systems require multiple tunnels to be drilled per bone in order to achieve final fixation, which can weaken the bone(s). Current systems require retrieval of the suture at or very near the plantar plate, which can be very tedious and time consuming in the operating room.

Thus, there is a need for apparatus, systems, and methods for plantar plate repair that are compact, maneuverable, and simple. There is a need for a system that uses a single bone tunnel per bone so that no extra bone preparation steps are necessary, thus saving operative time and maintaining greater bone strength versus systems that use multiple bone tunnels. A system that enables retrieval of the free ends of the suture outside the surgical opening or incision is less tedious and saves operative time.

SUMMARY

The various systems and methods of the present technology have been developed in response to the present state of the art, and in particular, in response to the problems and needs in the art that have not yet been fully solved by currently available plantar plate repair systems.

In an aspect of the technology, a kit for plantar plate repair includes an implant assembly including an implant, an implant inserter, a first suture shuttle, and a second suture shuttle, wherein the implant includes a dorsal head, a body extending from the head, a first longitudinal cannulation, and a second longitudinal cannulation beside the first longitudinal cannulation, wherein the implant inserter is coupled to the dorsal head of the implant, wherein the first suture shuttle extends within the first longitudinal cannulation, wherein the second suture shuttle extends within the second longitudinal cannulation, wherein the first and second suture shuttles protrude from a plantar end of the implant opposite the dorsal head.

Embodiments of the technology may include any or all of the following attributes. The implant inserter includes a third longitudinal cannulation, wherein the first suture shuttle extends within the third longitudinal cannulation. The second suture shuttle extends within the third longitudinal cannulation. The implant inserter includes a fourth longitudinal cannulation, wherein the second suture shuttle extends within the fourth longitudinal cannulation. The first and second suture shuttles each include a loop and a heel opposite the loop, wherein the heels of the first and second suture shuttles are fixed to a handle, wherein the handle is coupled to an opposite end of the implant inserter from the implant, wherein the loops of the first and second suture shuttles protrude from the plantar end of the implant. The kit may include a needle assembly including a needle and a needle threader, wherein the needle includes a point, a heel opposite the point, and at least one eye through the heel, wherein the needle threader includes a handle and a loop opposite the handle, wherein the needle threader extends through the eye so that the handle and loop extend from opposite sides of the needle. The kit may include a needle caddy, wherein the needle caddy covers at least the point of the needle and supports the needle threader. The kit may include a needle driver; a distractor; a first k-wire; a second k-wire, wherein the second k-wire has a larger outer diameter than the first k-wire; and a packaging tray.

In another aspect of the technology, a method for plantar plate repair includes exposing a metatarsophalangeal joint, wherein the metatarsophalangeal joint includes a metatarsal, a proximal phalanx, a plantar plate, and a flexor tendon; reflecting a plantar plate from the proximal phalanx and the flexor tendon; distracting the metatarsophalangeal joint; passing a suture through a distal portion of the plantar plate; forming only one bone tunnel through a proximal epiphysis of the proximal phalanx; providing an implant assembly, wherein the implant assembly includes an implant, an implant inserter coupled to a dorsal end of the implant, a first suture shuttle, and a second suture shuttle, wherein the implant includes a dorsal head, a first longitudinal cannulation, and a second longitudinal cannulation beside the first longitudinal cannulation, wherein the first suture shuttle extends within the first longitudinal cannulation, wherein the second suture shuttle extends within the second longitudinal cannulation, wherein the first and second suture shuttles protrude from a plantar end of the implant opposite the dorsal head; passing the first and second suture shuttles through the bone tunnel; passing a first free end of the suture through the first suture shuttle; passing a second free end of the suture through the second suture shuttle; passing the first free end of the suture through the bone tunnel and the first longitudinal cannulation by pulling a proximal end of the first suture shuttle; passing the second free end of the suture through the bone tunnel and the second longitudinal cannulation by pulling a proximal end of the second suture shuttle; advancing the plantar end of the implant into the bone tunnel until the dorsal head rests against the proximal phalanx; decoupling the implant inserter from the dorsal end of the implant; reducing the proximal phalanx relative to the metatarsal; tensioning the suture; tying a knot in the suture, the knot resting against the dorsal head of the implant; and closing the exposure of the metatarsophalangeal joint.

Embodiments of the technology may include any or all of the following attributes. The first and second free ends of the suture are passed through the first and second suture shuttles, respectively, outside of the metatarsophalangeal joint. The proximal ends of the first and second suture shuttles are pulled simultaneously. The method may include inserting a first k-wire through the distal epiphysis of the metatarsal; inserting a second k-wire through the proximal epiphysis of the proximal phalanx; coupling a first arm of a distractor to the first k-wire; coupling a second arm of the distractor to the second k-wire; threading an eye of a needle with the suture; passing the suture through the distal portion of the plantar plate with the needle; removing the second k-wire from the proximal phalanx, leaving the bone tunnel through the proximal phalanx; and removing the first k-wire from the distal epiphysis of the metatarsal, leaving a hole through the distal epiphysis of the metatarsal. The method may include creating a Weil osteotomy of a distal epiphysis of the metatarsal; temporarily fixing a distal capital fragment of the metatarsal to a plantar aspect of the distal epiphysis of the metatarsal; removing the temporary fixation of the distal capital fragment of the metatarsal to the distal epiphysis of the metatarsal; reducing the distal capital fragment of the metatarsal against the distal epiphysis of the metatarsal; and securing the distal capital fragment of the metatarsal to the distal epiphysis of the metatarsal. The method may include inserting the first k-wire through the distal epiphysis of the metatarsal and into the distal capital fragment of the metatarsal to temporarily fix the distal capital fragment of the metatarsal to the distal epiphysis of the metatarsal; and removing the first k-wire from the distal epiphysis of the metatarsal and the distal capital fragment of the metatarsal, so that the hole extends through the distal epiphysis of the metatarsal and the distal capital fragment of the metatarsal.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Proximal means toward the trunk, or, in the case of an inanimate object, toward a user. Distal means away from the trunk, or, in the case of an inanimate object, away from a user. Dorsal means toward the top of the foot. Plantar means toward the sole of the foot. Ipsilateral means on the same side of the body. Contralateral means on the opposite side of the body. These descriptive terms may be applied to an animate or inanimate body.

Figure 1:
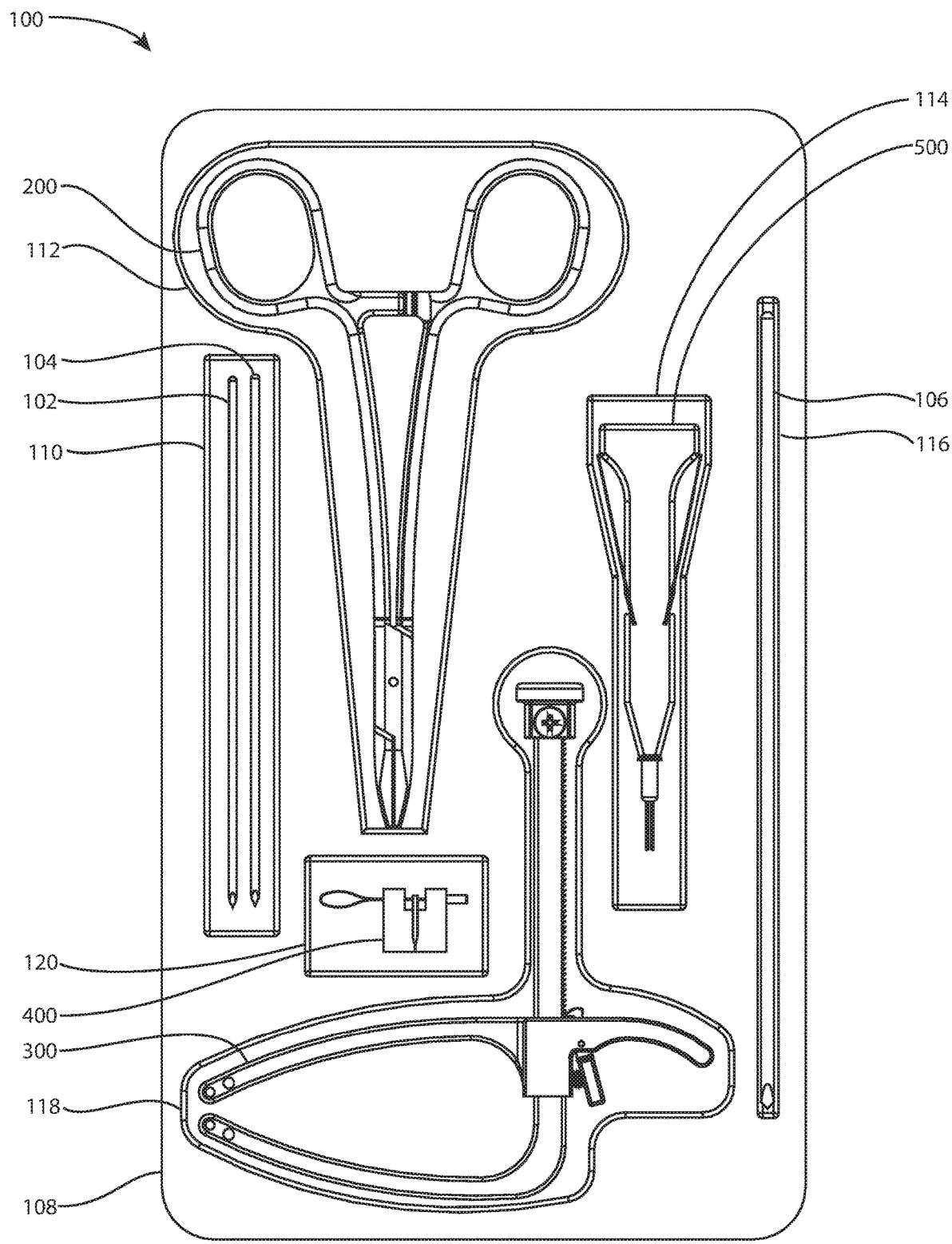
FIG. 1 is a top view of a kit for plantar plate repair.

Referring to FIG. 1, a kit 100 for plantar plate repair includes an implant assembly 500. The kit 100 may include a first k-wire 102, a second k-wire 104, a third k-wire 106, a needle driver 200, a distractor 300, and/or a needle assembly 400. The kit 100 may include at least one packaging tray 108 for organizing and protecting the other contents of the kit 100. The kit 100 may include a bone screw 124 (FIG. 19), a driver 126 for the bone screw (FIG. 19), a lid (not shown) for the tray 108, and/or an outer carton or box (not shown) to contain the kit contents in the tray 108.

The first and second k-wires 102, 104 are preferably 1.6 mm in diameter with trocar tips, although smaller or larger diameters and/or other tip configurations are also suitable.

The third k-wire 106 is preferably 2.5 mm in diameter with a trocar tip, although smaller or larger diameters and/or other tip configurations are also suitable. The third k-wire may be a Steinmann pin or a drill bit.

Figure 2A:
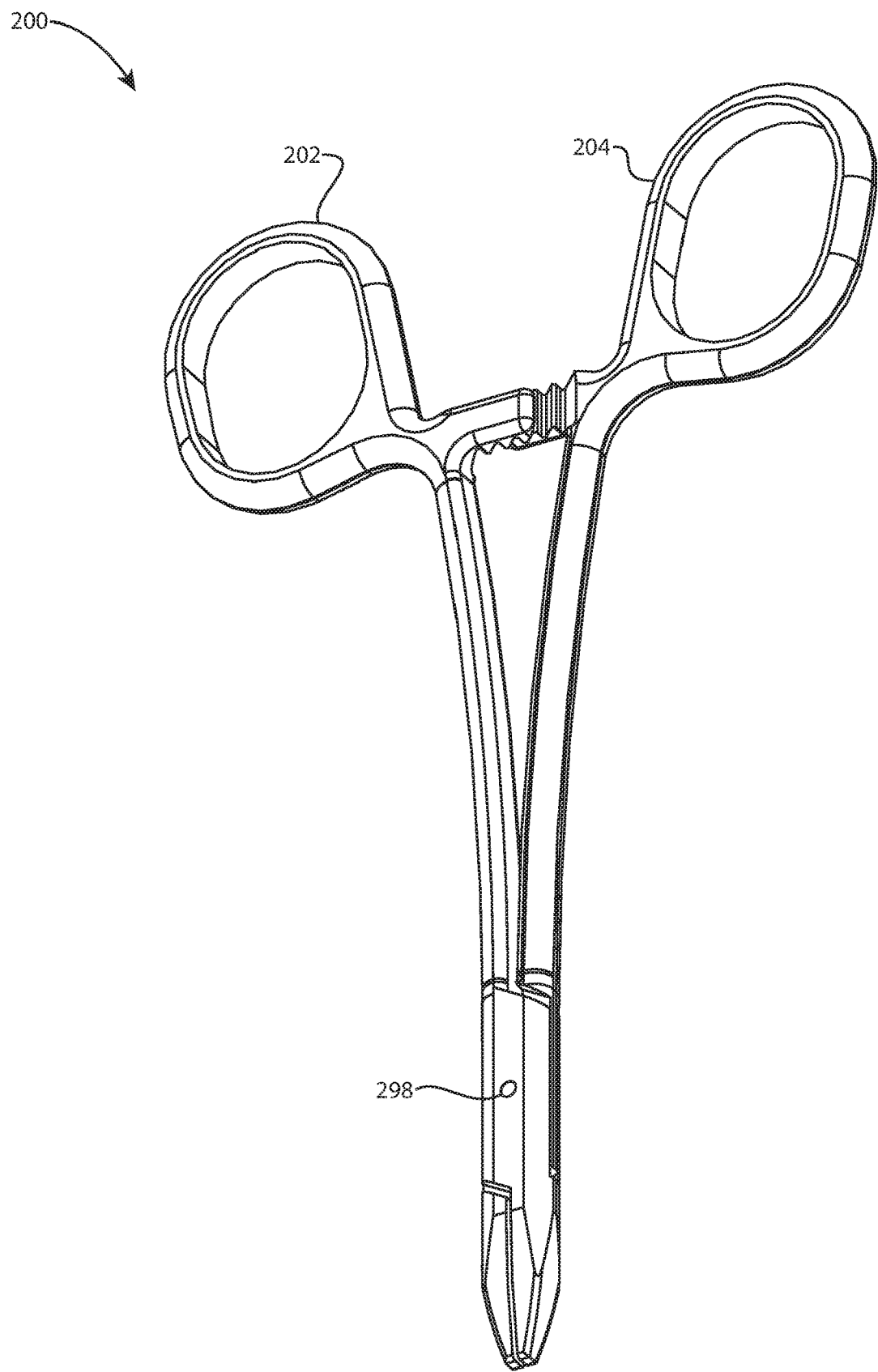
FIG. 2A is an isometric view of a needle driver of the kit of FIG. 1.
Figure 2B:
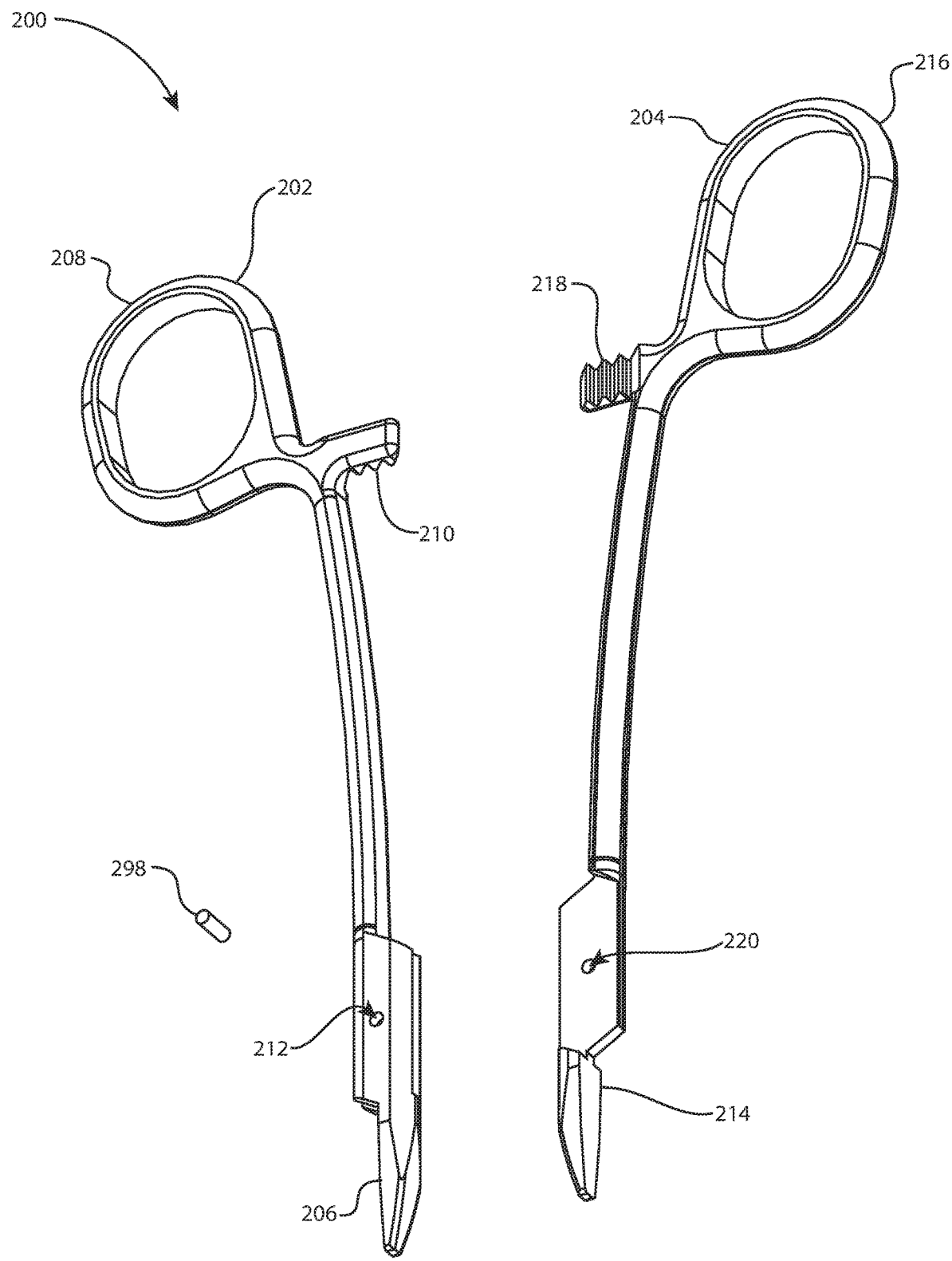
FIG. 2B is an exploded isometric view of the needle driver of FIG. 2A.
Figure 2C:
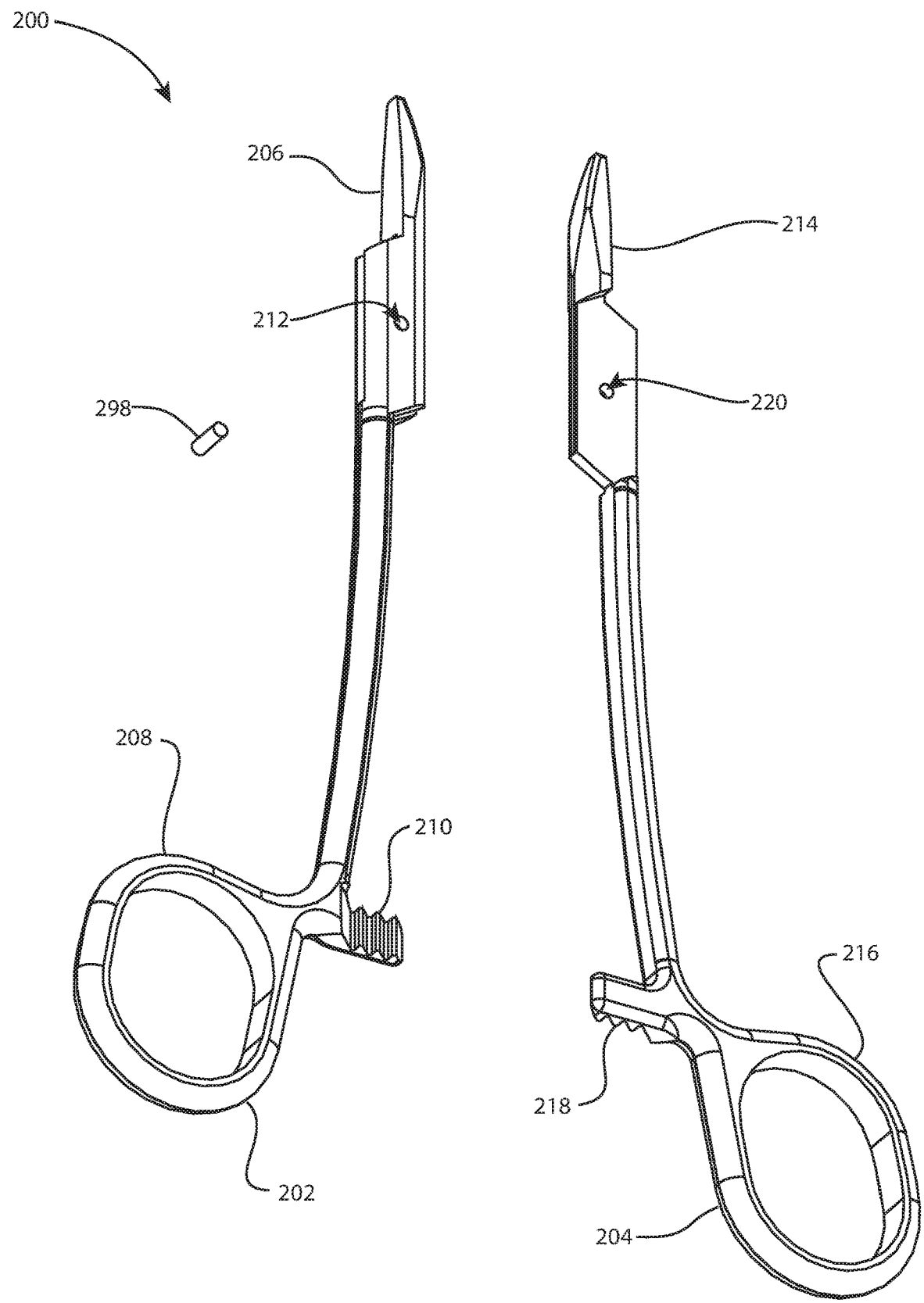
FIG. 2C is another exploded isometric view of the needle driver of FIG. 2A, from a different viewpoint.

Referring to FIGS. 2A-2C, the needle driver 200 includes a first body 202, a second body 204, and a pin 298. The needle driver 200 may resemble a hemostat, or may be a hemostat. The needle driver 200 is used to grasp and manipulate a needle to pass sutures through the plantar plate.

The first body 202 includes a first jaw 206, a first handle 208 at an opposite end of the first body 202 from the first jaw 206, a first ratchet 210 near the first handle 208, and a first hole 212 between the first jaw 206 and the first handle 208.

The second body 204 includes a second jaw 214, a second handle 216 at an opposite end of the second body 204 from the second jaw 214, a second ratchet 218 near the second handle 216, and a second hole 220 between the second jaw 214 and the second handle 216.

The first and second bodies 202, 204 are hinged together by the pin 298 through the first and second holes 212, 220 so that the first and second jaws 206, 214 face each other, the first and second ratchets 210, 218 face each other, and the first and second handles 208, 216 face away from each other. The first and second jaws 206, 214 cooperate to grasp a needle. When the second handle 216 is rotated toward the first handle 208, the second jaw 214 rotates toward the first jaw 206 and the second ratchet 218 rotates toward the first ratchet 210. When the second handle 216 is close to the first handle 208, the second ratchet 218 engages the first ratchet 210 to prevent the second handle 216 from rotating away from the first handle 208, thus preventing the second jaw 214 from rotating away from the first jaw 206. However, the engaged first and second ratchets 210, 218 may permit the second handle 216 to rotate toward the first handle 208, thus permitting the second jaw 214 to rotate toward the first jaw 206 until the second jaw 214 contacts the first jaw 206. The first and second ratchets 210, 218 may be disengaged by moving the second ratchet 218 laterally away from the first ratchet 210, for example by twisting the second handle 216 relative to the first handle 208.

Figure 3A:
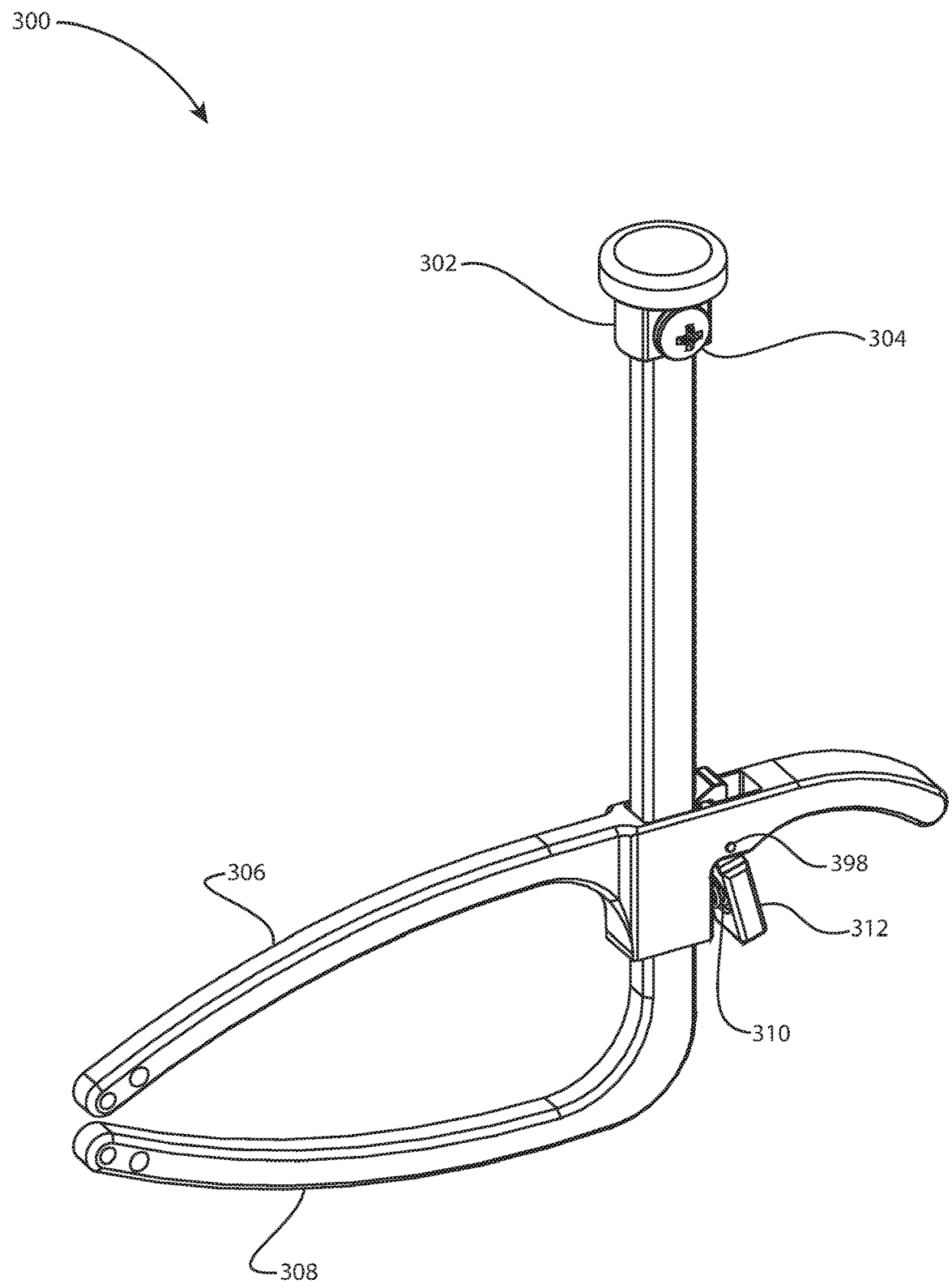
FIG. 3A is an isometric view of a distractor of the kit of FIG. 1.
Figure 3B:
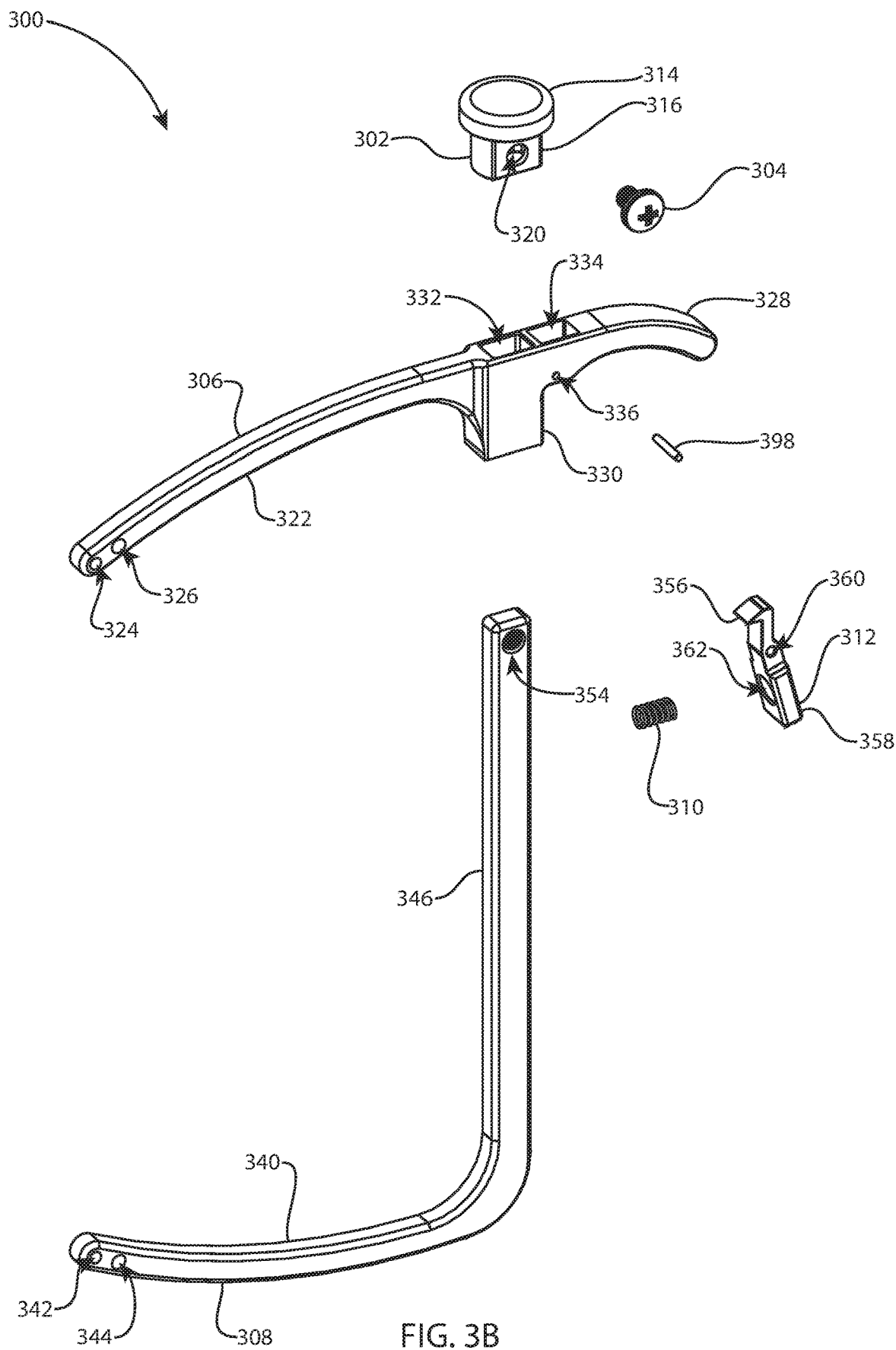
FIG. 3B is an exploded isometric view of the distractor of FIG. 3A.
Figure 3C:
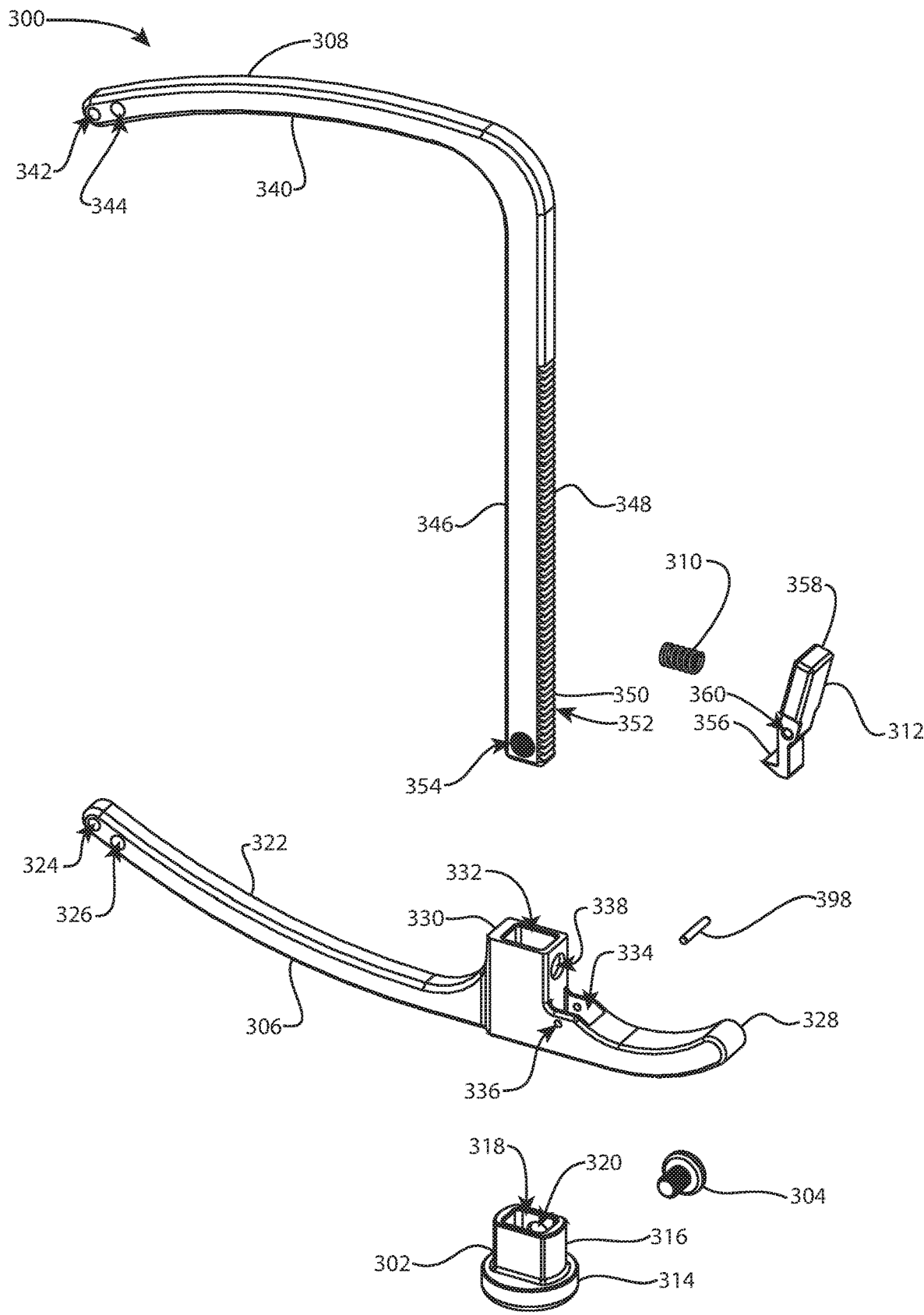
FIG. 3C is another exploded isometric view of the distractor of FIG. 3A, from a different viewpoint.

Referring to FIGS. 3A-3C, the distractor 300 includes a cap 302, a screw 304, a first body 306, a second body 308, a spring 310, a pawl 312, and a pin 398. The distractor 300 is used to distract the metacarpophalangeal joint during plantar plate repair surgery.

The cap 302 includes a broad head 314, a shaft 316 extending from the head 314, a socket 318 extending within the shaft 316 toward the head 314, and a hole 320 extending transversely through the shaft 316 to intersect the socket 318. The socket 318 receives a portion of the second body 308 and the hole 320 receives the screw 304.

The first body 306 includes an elongated first arm 322 with at least one hole 324 extending transversely through the first arm 322. An optional second hole 326 is illustrated. The first hole 324 may be sized to receive the first or second k-wire 102, 104. The second hole 326 may be sized to receive the third k-wire 106 or a smaller or larger pin or drill bit. The first body 306 includes a protrusion 328 which extends opposite to the first arm 322 and a shaft portion 330 between the first arm 322 and the protrusion 328. The shaft portion 330 includes a first aperture 332, or through hole, which receives a portion of the second body 308. The shaft portion 330 includes a second aperture 334, or through hole, which receives a portion of the pawl 312. A transverse hole 336 extends through the shaft portion to intersect the second aperture 334. The hole 336 receives the pin 398. Another transverse hole 338 extends through the shaft portion toward the first aperture 332, however hole 338 may be a blind hole that does not intersect the first aperture 332. Hole 338 receives a portion of the spring 310.

The second body 308 includes an elongated second arm 340 with at least one hole 342 extending transversely through the second arm. An optional second hole 344 is illustrated. The first hole 342 may be sized to receive the first or second k-wire 102, 104. The second hole 344 may be sized to receive the third k-wire 106 or a smaller or larger pin or drill bit. The second body 308 includes a shaft portion 346 that extends from the second arm 340 so that the second body 308 appears L-shaped. The shaft portion 346 includes a linear rack 348 with alternating teeth 350 and grooves 352. The shaft portion 346 includes a transverse threaded hole 354 through an end opposite to the second arm 340. The shaft portion 346 is received through the first aperture 332 of the first body 306 and in the socket 318 of the cap 302 so that the hole 354 aligns with the hole 320. The screw 304 extends through the hole 320 and threads into the hole 354 to secure the cap 302 to the second body 308.

The pawl 312 includes a tooth 356 which engages the rack 348 of the second body 308, a lever 358 at an opposite end of the pawl 312 from the tooth 356, a transverse hole 360 that extends through the pawl 312 between the tooth 356 and the lever 358, and a blind hole 362 that extends into the lever 358. The hole 360 receives the pin 398. The hole 362 receives a portion of the spring 310.

The distractor 300 may be assembled by passing the shaft portion 346 of the second body 308 through the first aperture 332 of the first body 306 and into the socket 318 of the cap 302 so that the hole 354 of the second body 308 aligns with the hole 320 of the cap 302. The screw 304 extends through the hole 320 and threads into the hole 354 to secure the cap 302 to the second body 308. The pawl 312 is inserted into the second aperture 334 of the first body 306 so that the tooth 356 faces the rack 348 of the second body 308, the hole 362 faces the hole 338 of the first body 306, and the hole 360 aligns with the hole 336 of the first body. The pin 398 is inserted through the holes 336, 360 and the spring 310 is positioned with one end in hole 338 and the other end in hole 362 so that the pawl 312 is biased toward the rack 348. The pawl 312, pin 398, and spring 310 may be assembled to the first body 306 before the first body 306 is assembled to the second body 308, cap 302, and screw 304.

Figure 4A:
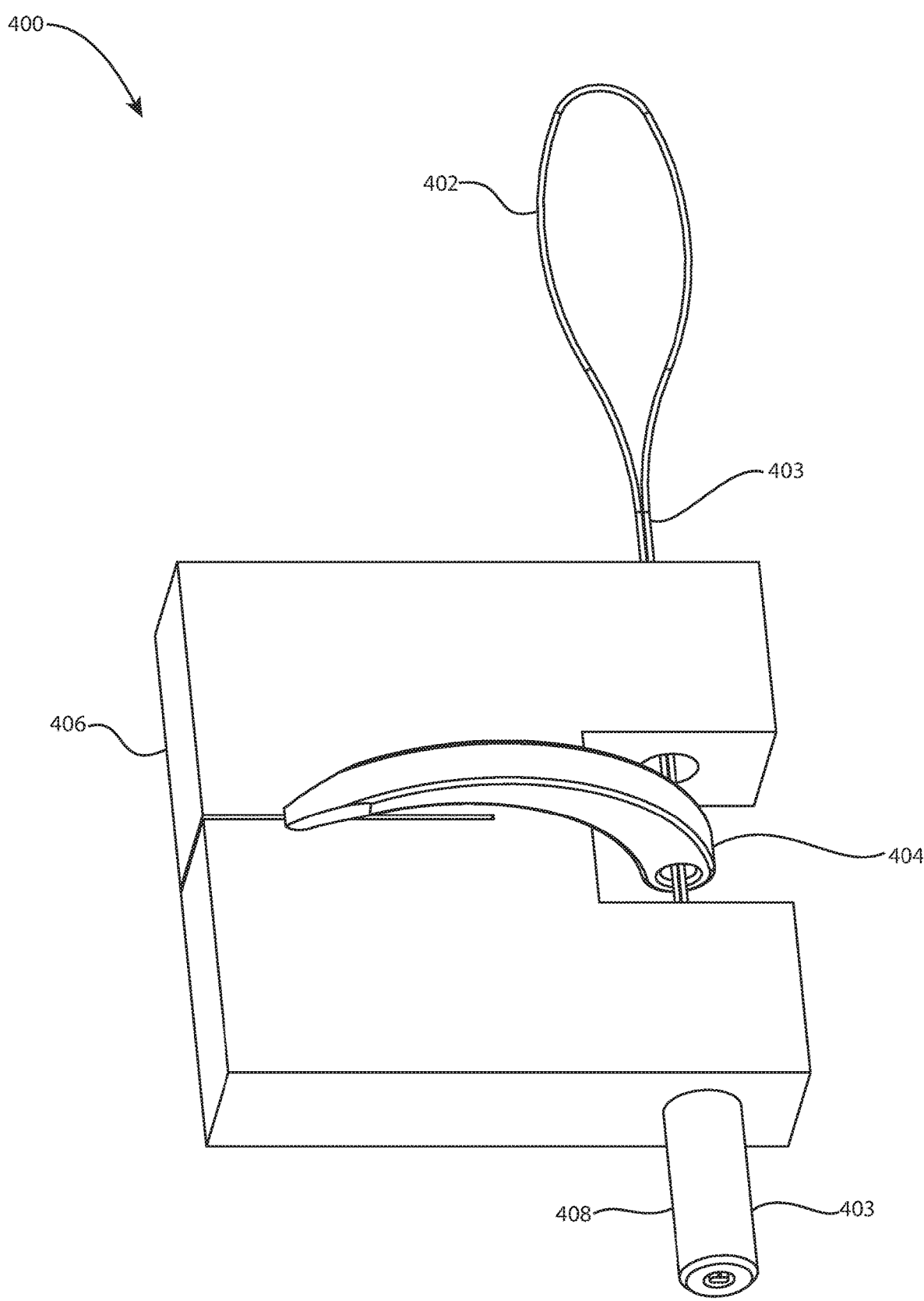
FIG. 4A is an isometric view of a needle assembly of the kit of FIG. 1.
Figure 4B:
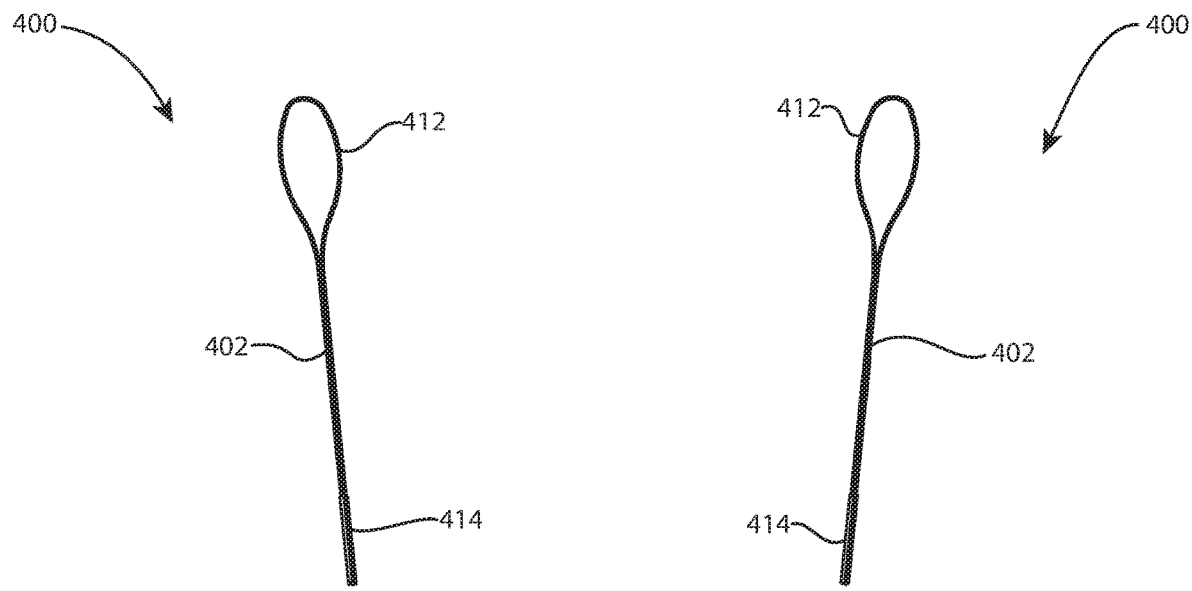
FIG. 4B is an exploded isometric view of the needle assembly of FIG. 4A.
Figure 4C:
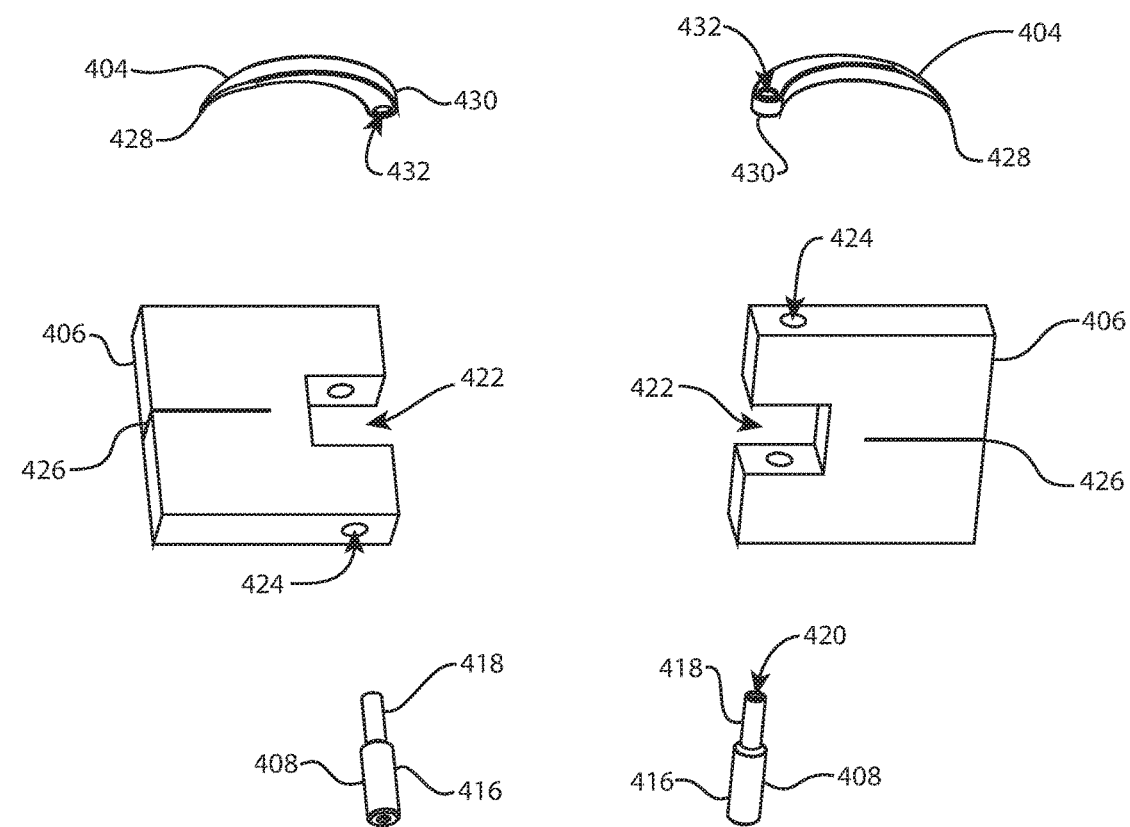
FIG. 4C is another exploded isometric view of the needle assembly of FIG. 4A, from a different viewpoint.
Figure 5A:
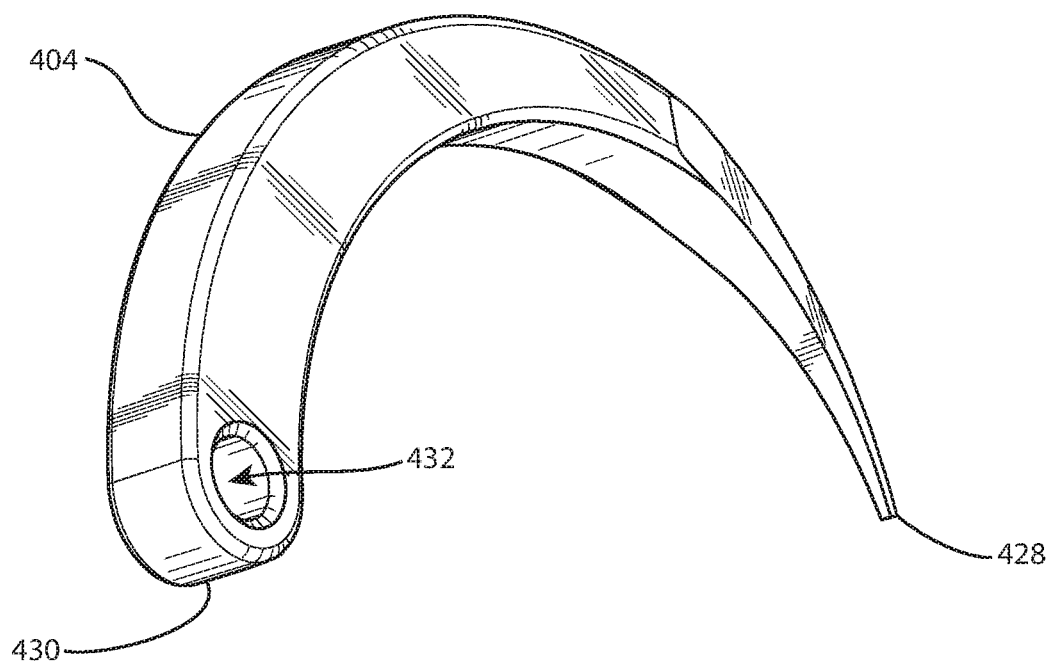
FIG. 5A is an isometric view of a needle of the needle assembly of FIG. 4A.
Figure 5B:
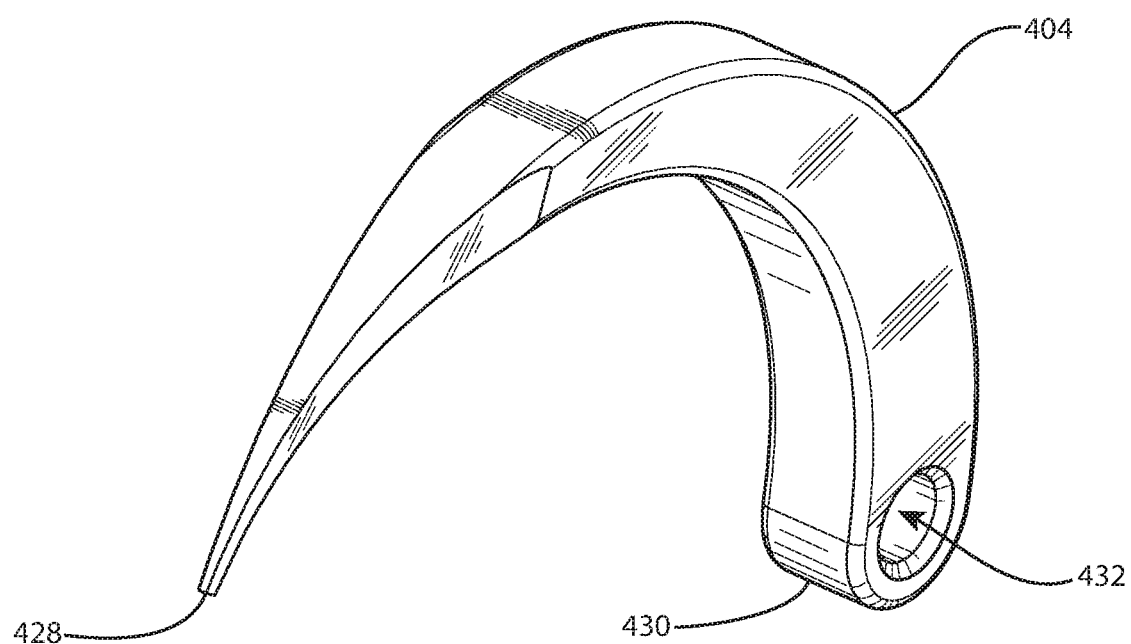
FIG. 5B is another isometric view of the needle of FIG. 5A, from a different viewpoint.
Figure 5C:
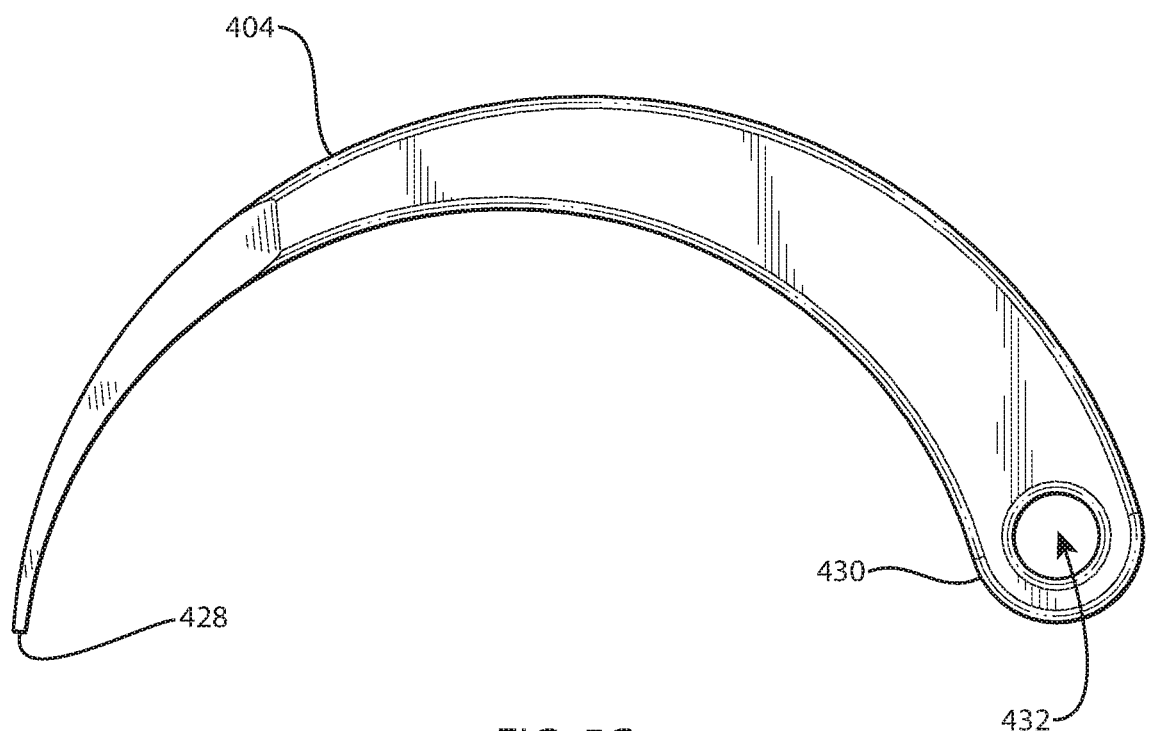
FIG. 5C is a front view of the needle of FIG. 5A.
Figure 5D:
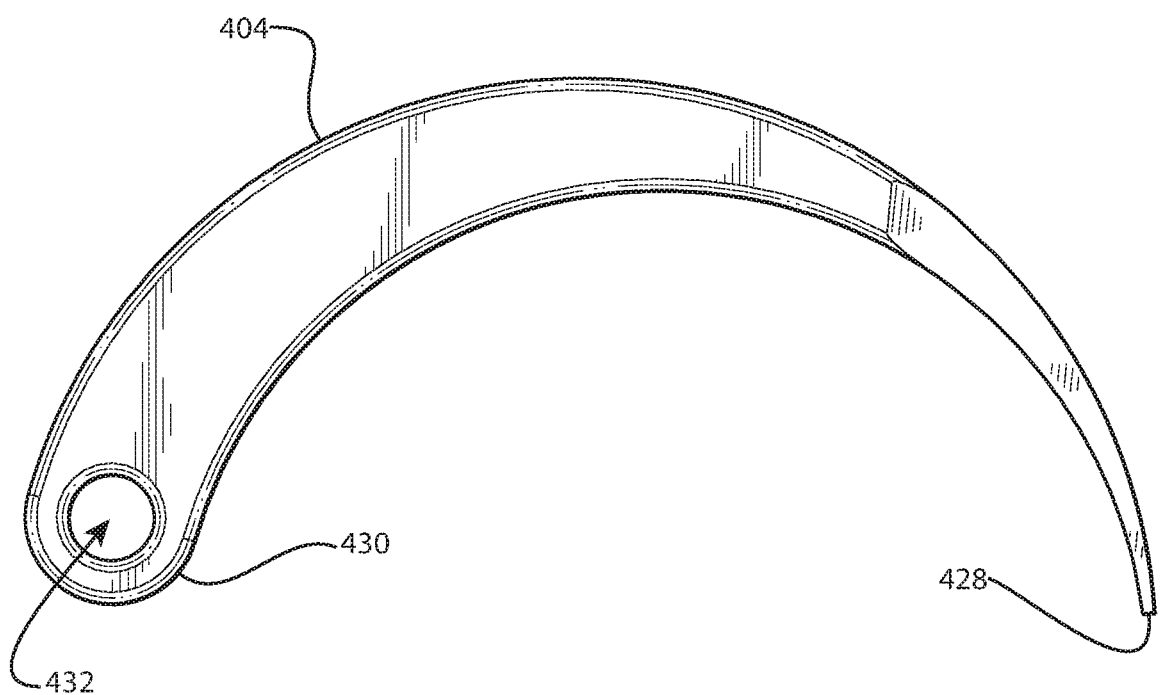
FIG. 5D is a back view of the needle of FIG. 5A.
Figure 5E:
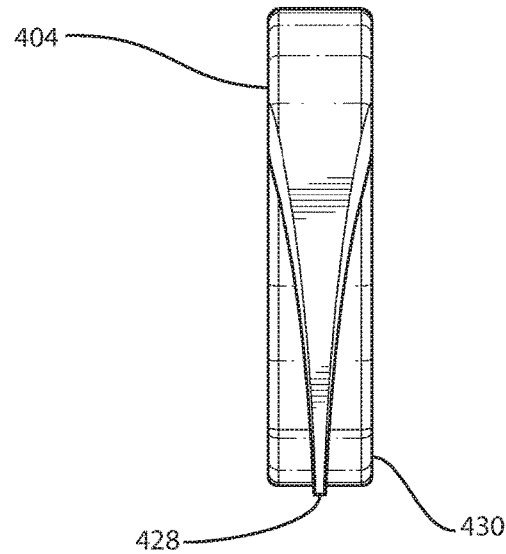
FIG. 5E is a left view of the needle of FIG. 5A.
Figure 5F:
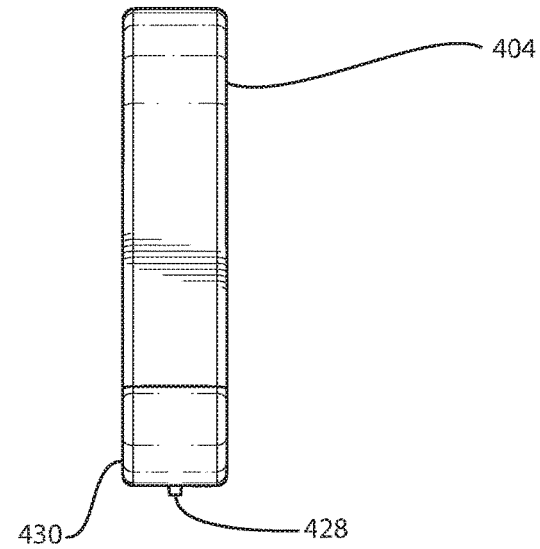
FIG. 5F is a right view of the needle of FIG. 5A.
Figure 5G:
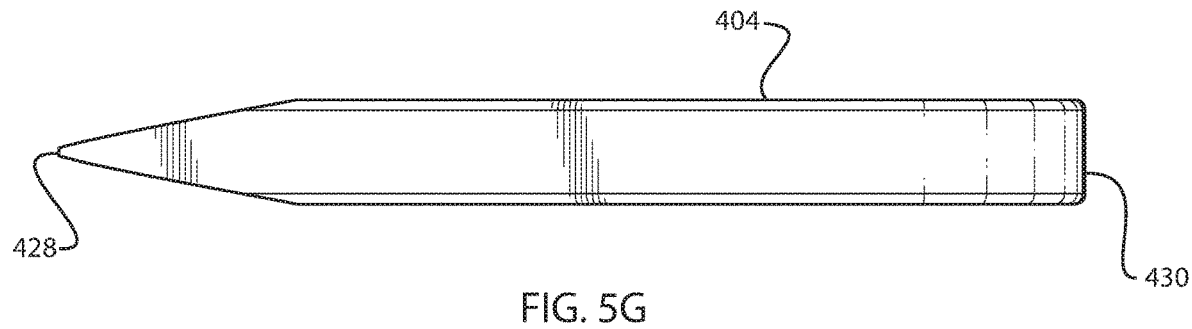
FIG. 5G is a top view of the needle of FIG. 5A.
Figure 5H:
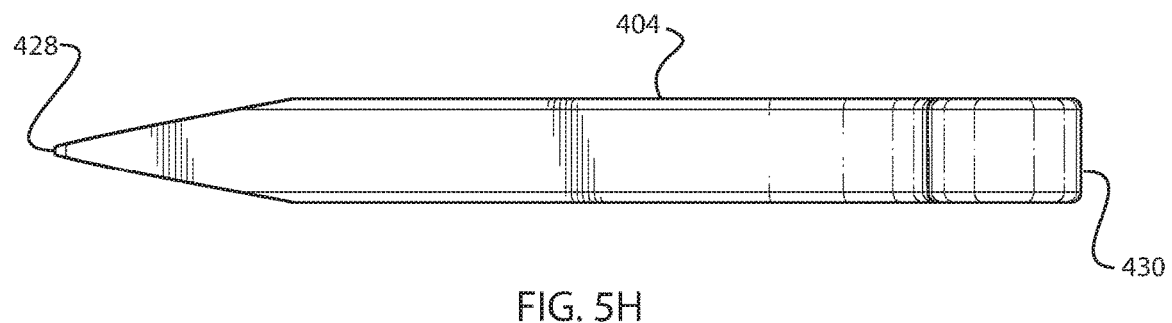
FIG. 5H is a bottom view of the needle of FIG. 5A.
Figure 6A:
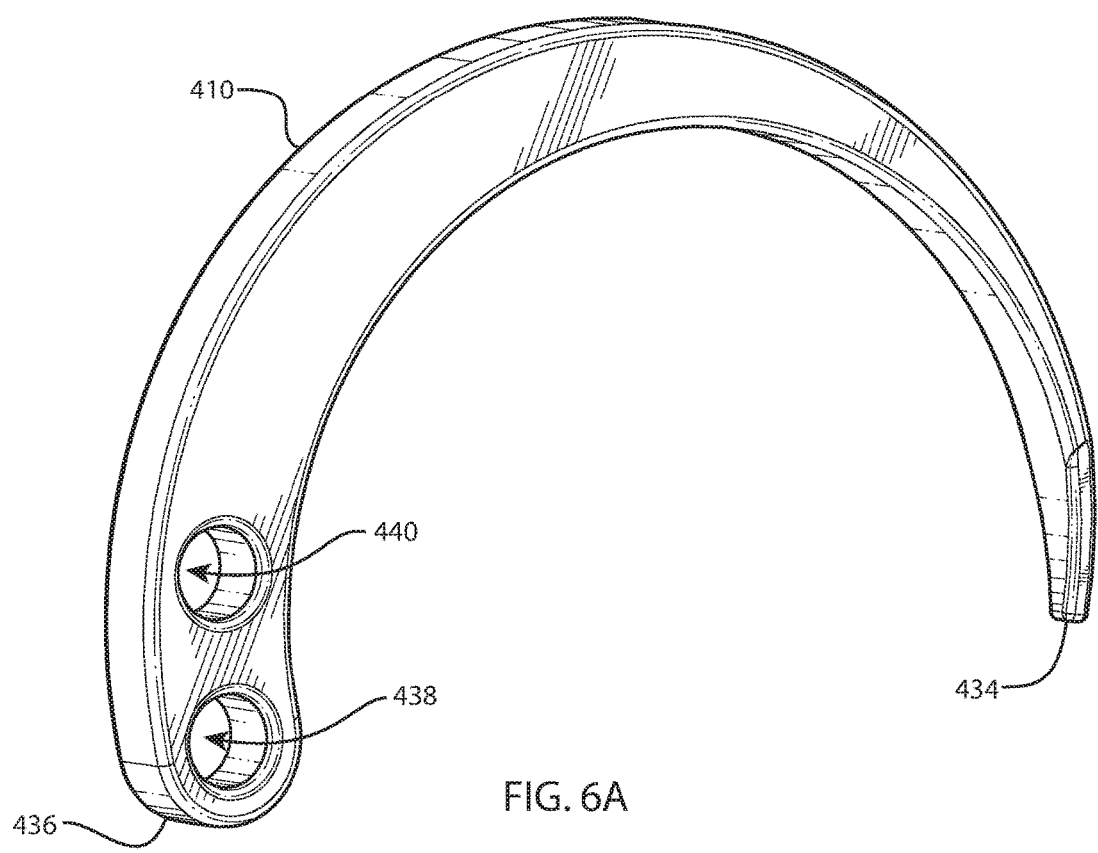
FIG. 6A is an isometric view of another needle.
Figure 6B:
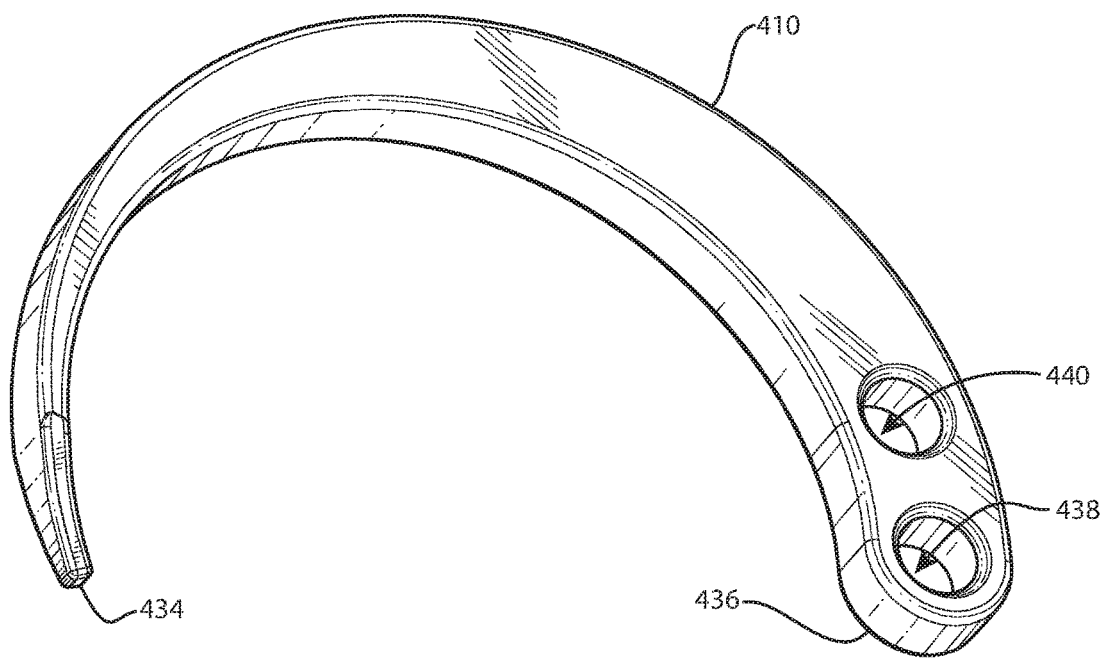
FIG. 6B is another isometric view of the needle of FIG. 6A, from a different viewpoint.
Figure 6C:
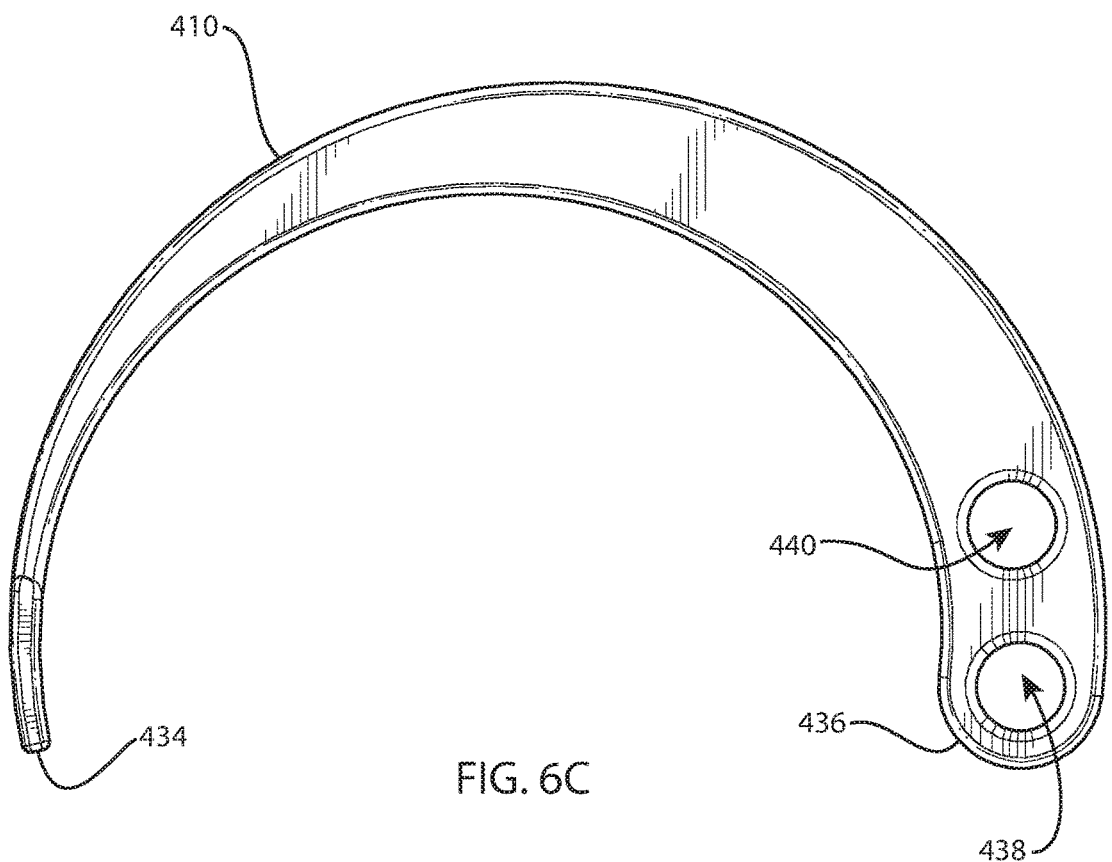
FIG. 6C is a front view of the needle of FIG. 6A.
Figure 6D:
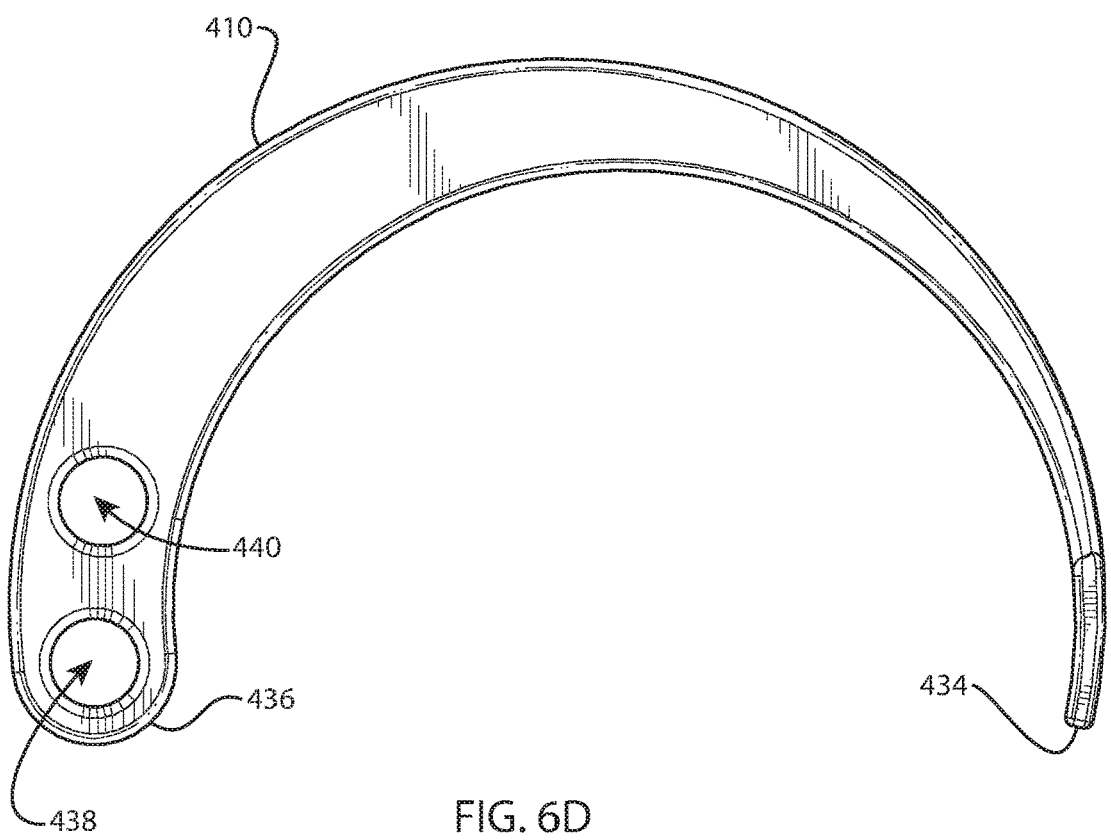
FIG. 6D is a back view of the needle of FIG. 6A.
Figure 6E:
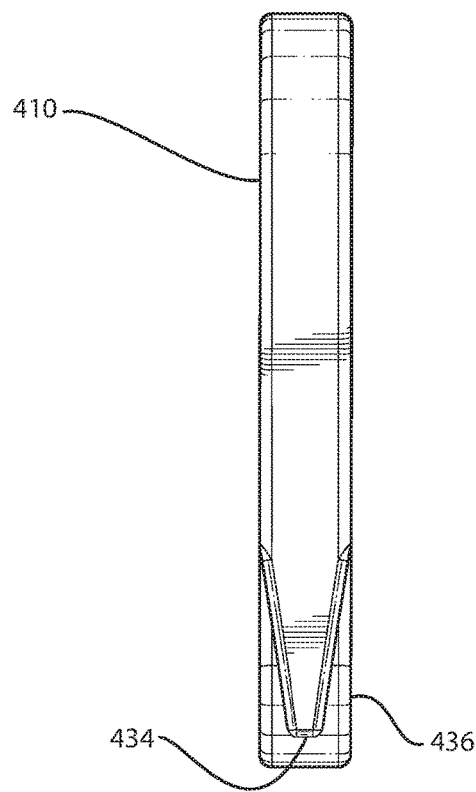
FIG. 6E is a left view of the needle of FIG. 6A.
Figure 6F:
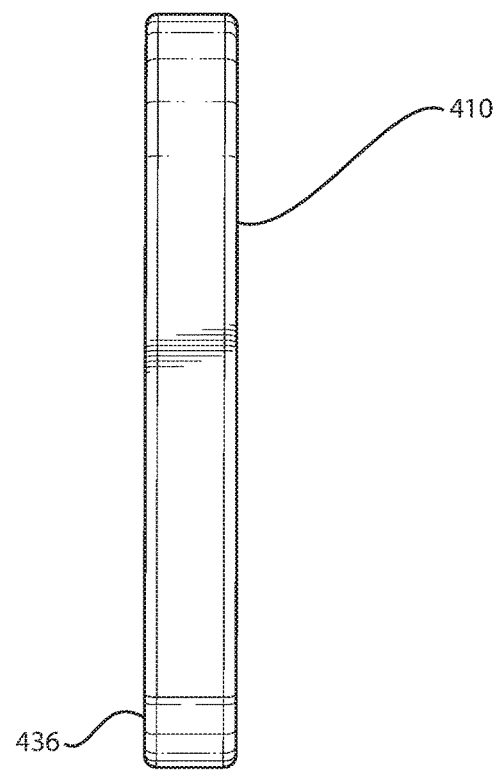
FIG. 6F is a right view of the needle of FIG. 6A.
Figure 6G:
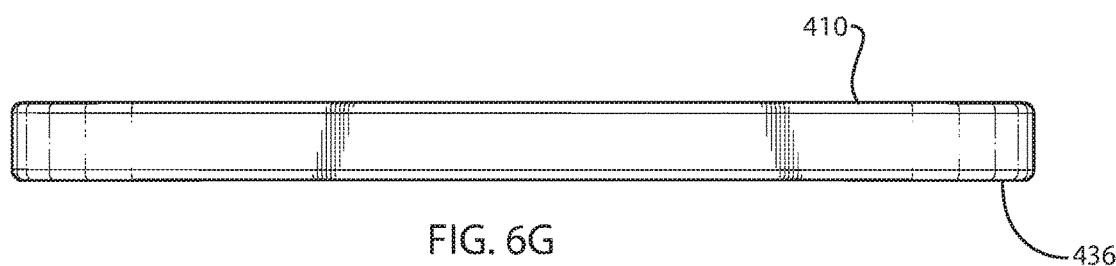
FIG. 6G is a top view of the needle of FIG. 6A.
Figure 6H:
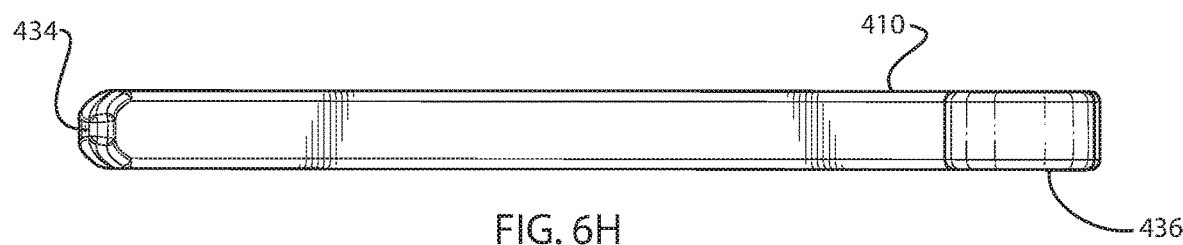
FIG. 6H is a bottom view of the needle of FIG. 6A.
Figure 7A:
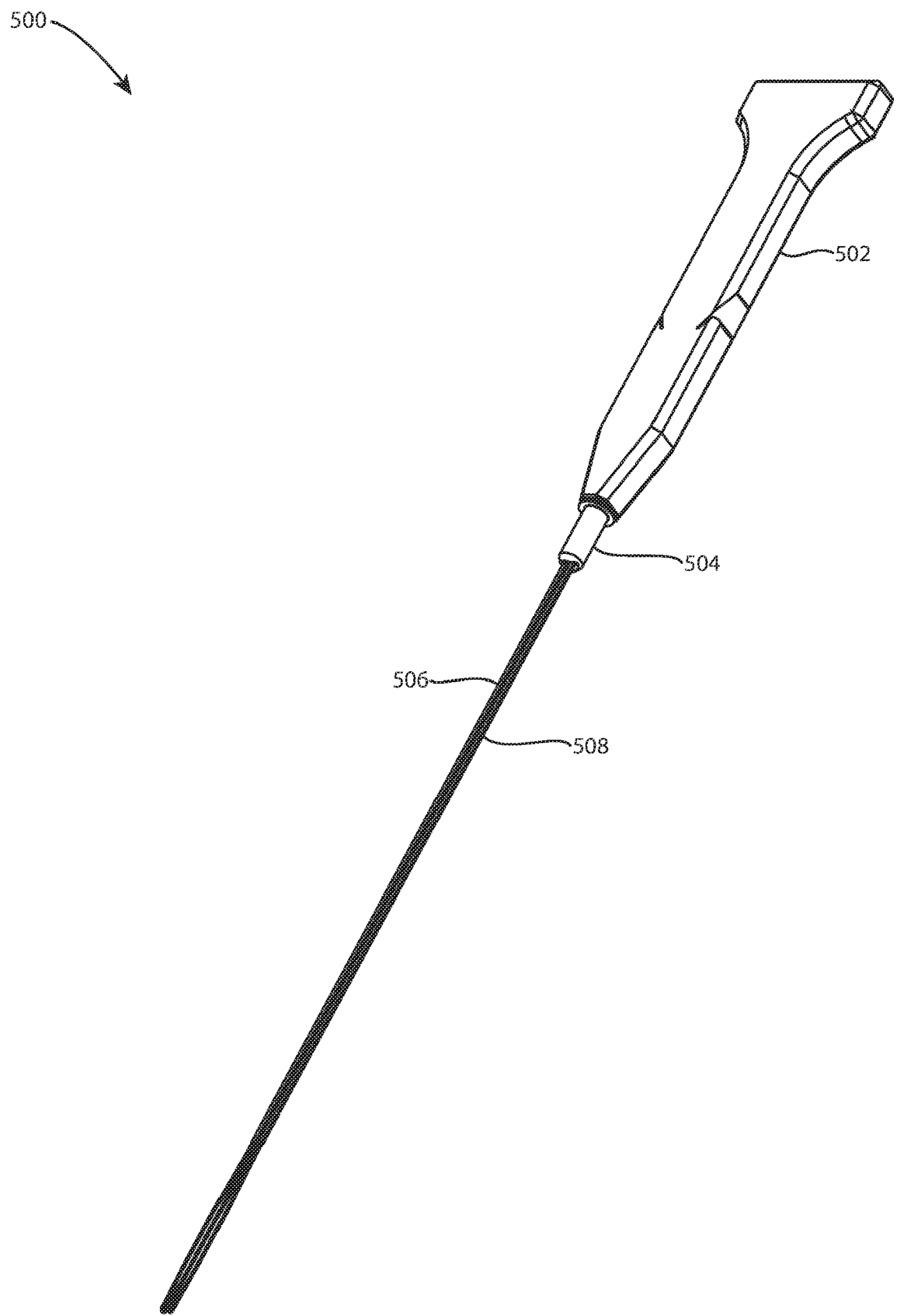
FIG. 7A is an isometric view of an implant assembly of the kit of FIG. 1 in a first configuration.
Figures 7B, 7C:
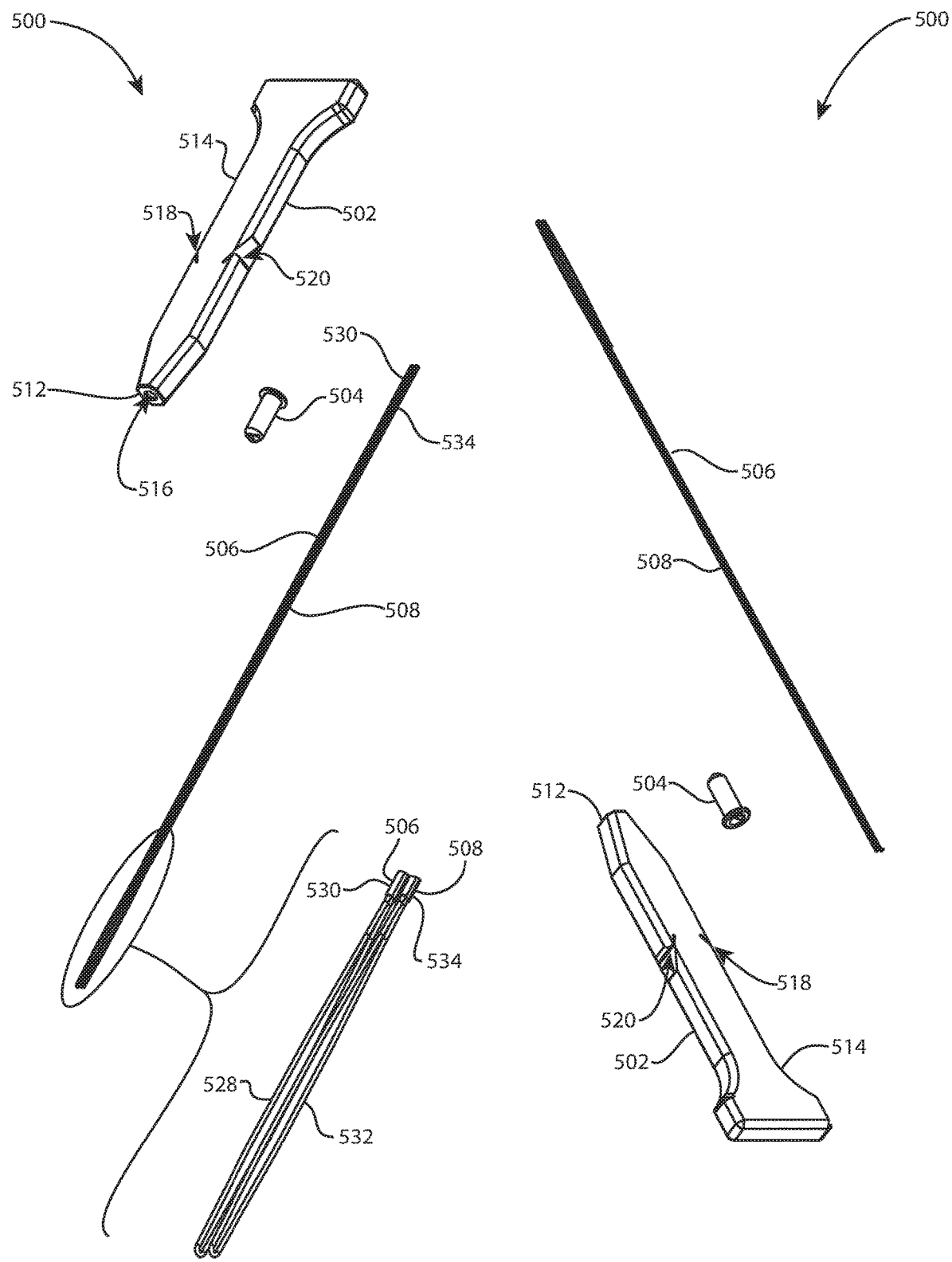
FIG. 7B is an exploded isometric view of the implant assembly of FIG. 7A.
FIG. 7C is another exploded isometric view of the implant assembly of FIG. 7A, from a different viewpoint.
Figure 7D:
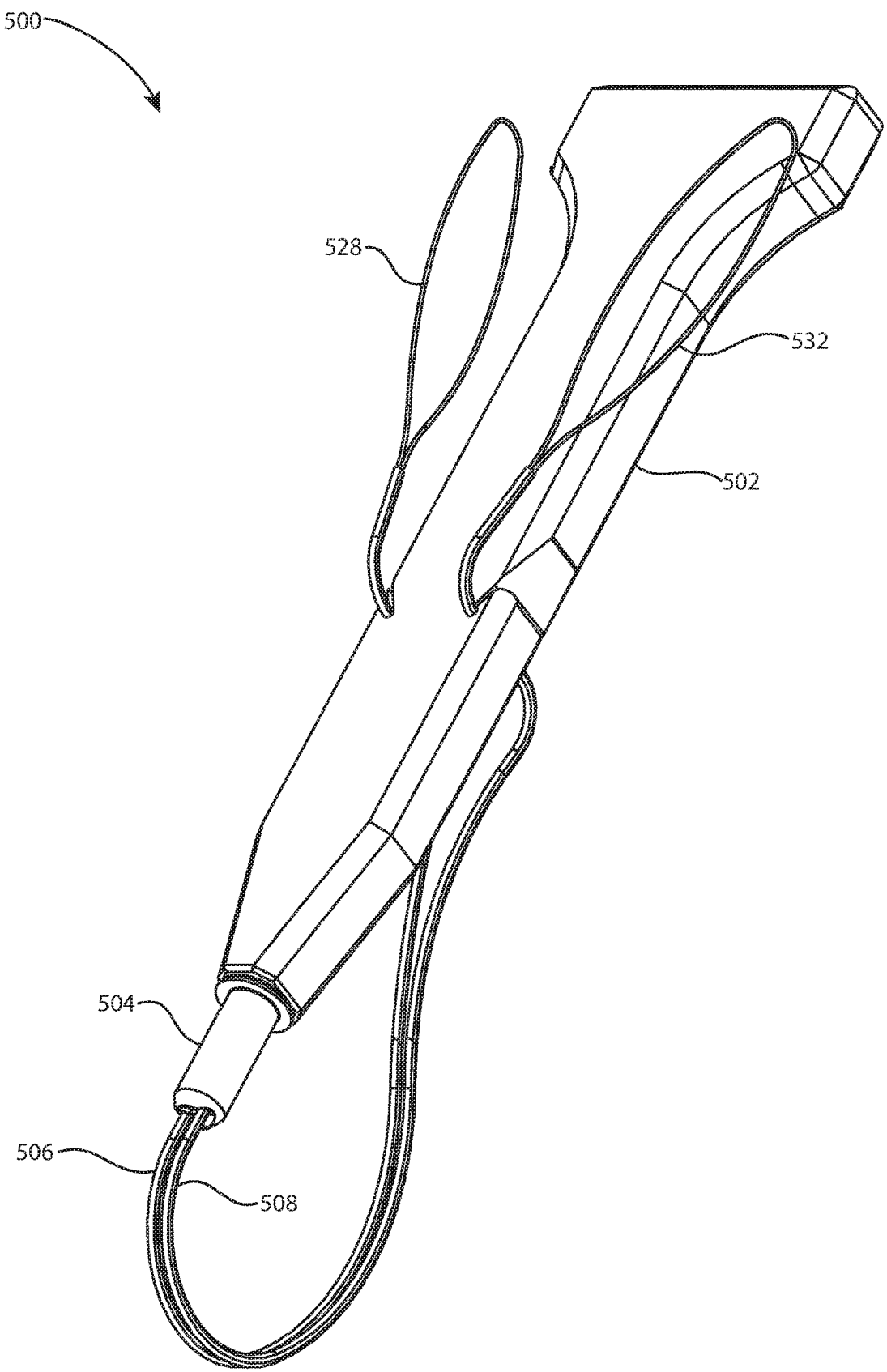
FIG. 7D is an isometric view of the implant assembly of FIG. 7A in a second configuration ready for use.
Figure 8A:
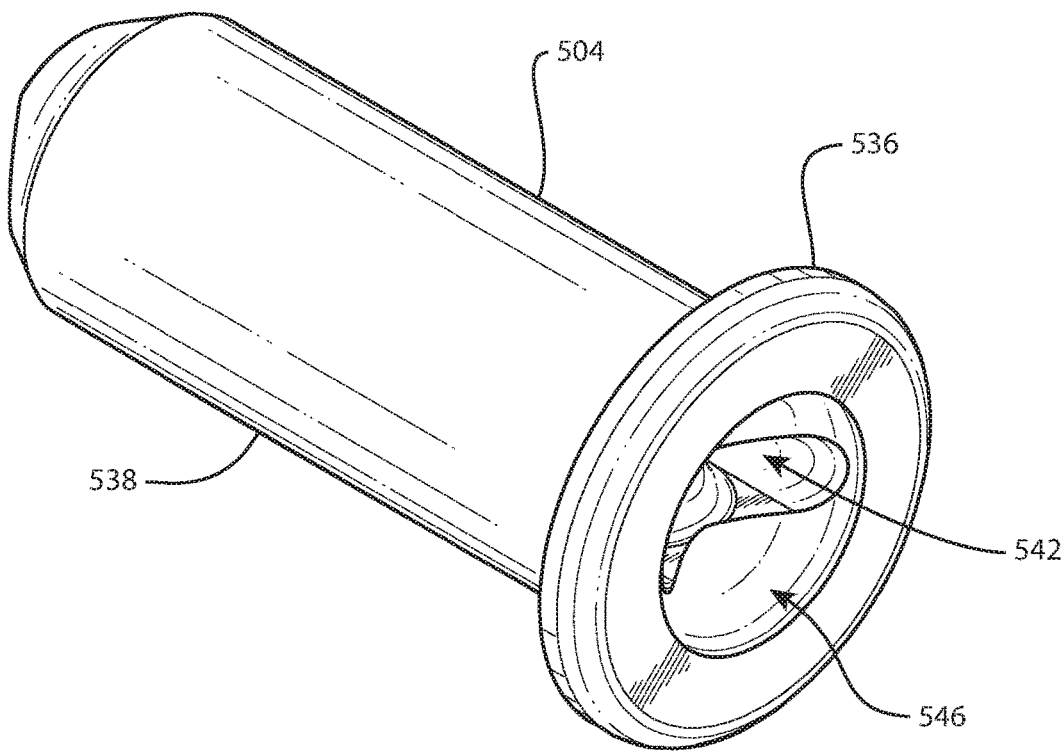
FIG. 8A is an isometric view of an implant of the implant assembly of FIG. 7A.
Figure 8B:
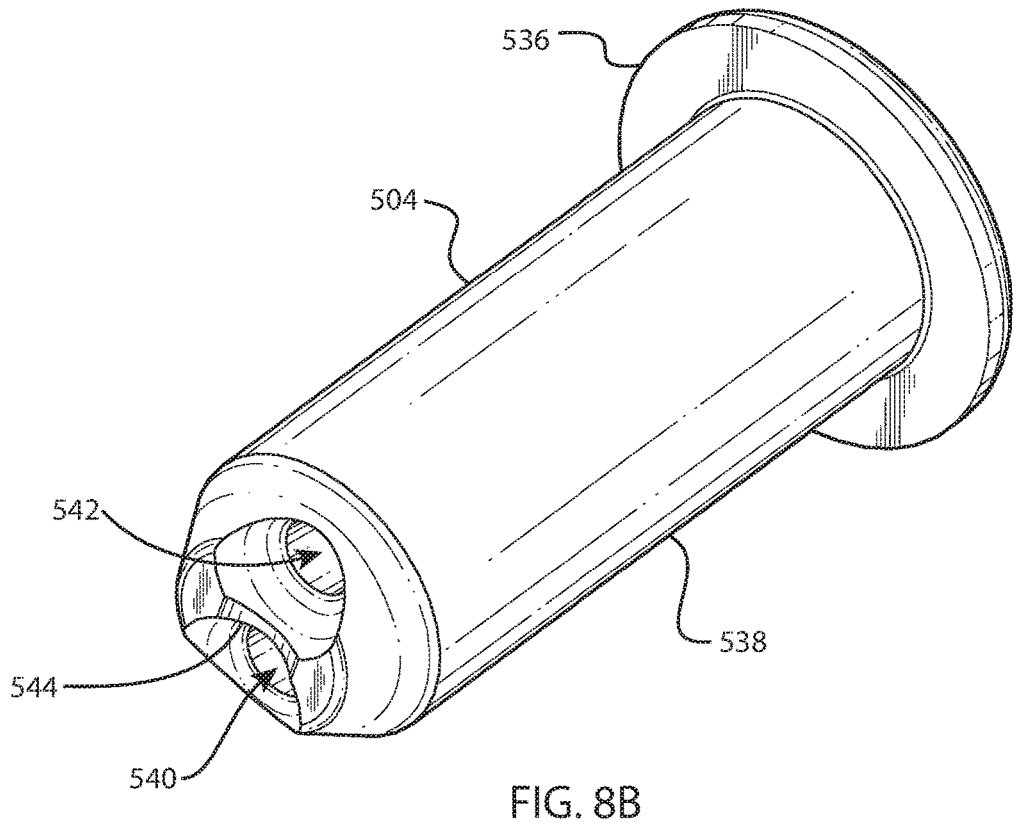
FIG. 8B is another isometric view of the implant of FIG. 8A, from a different viewpoint.
Figure 8C:
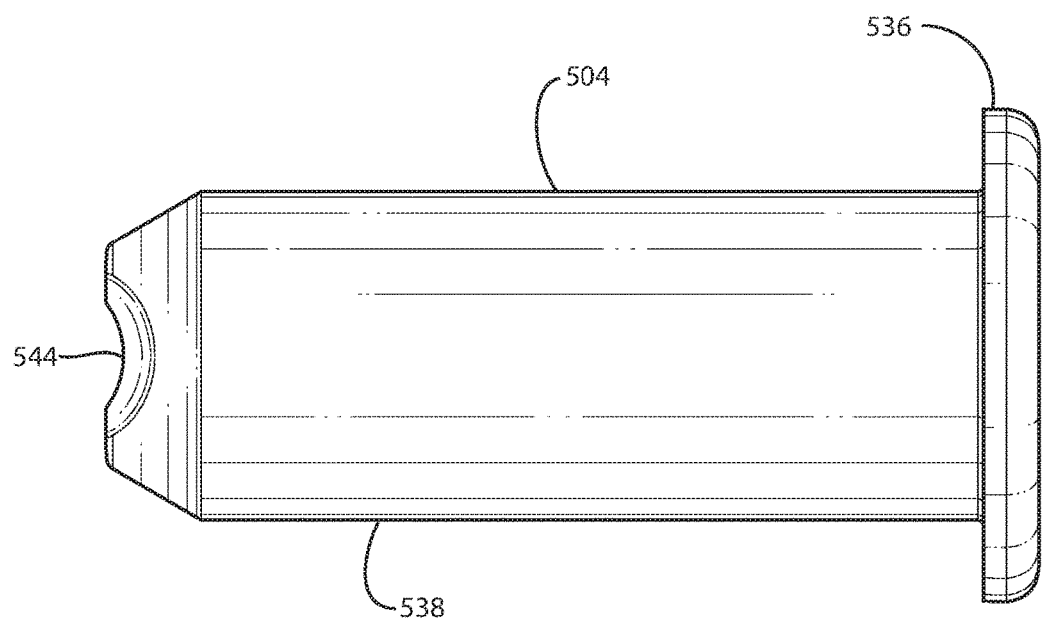
FIG. 8C is a front view of the implant of FIG. 8A.
Figure 8D:
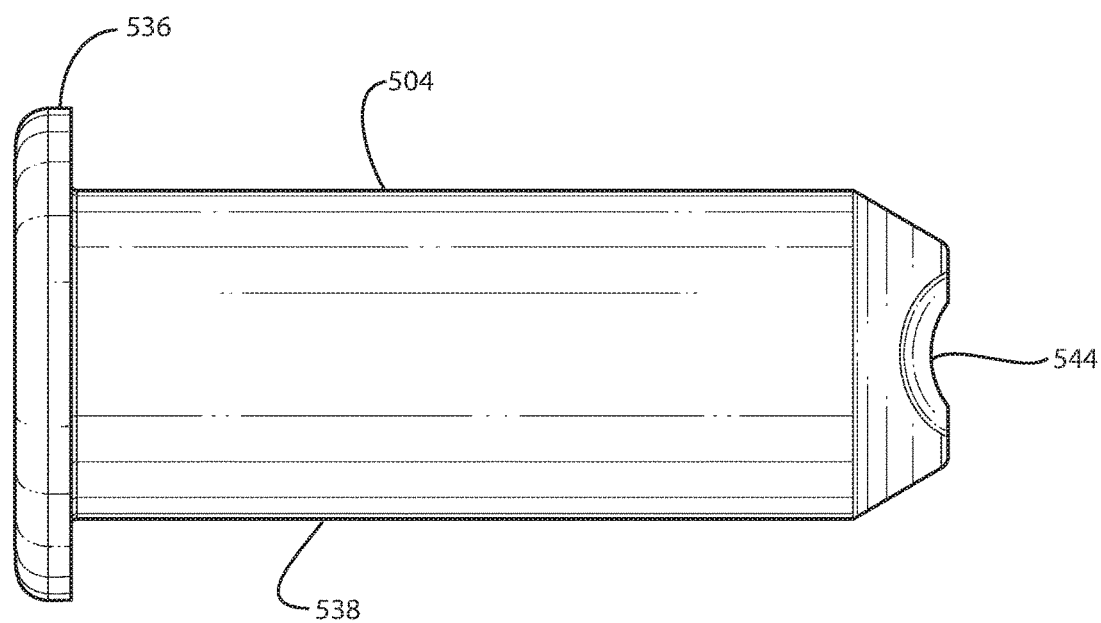
FIG. 8D is a back view of the implant of FIG. 8A.
Figure 8E:
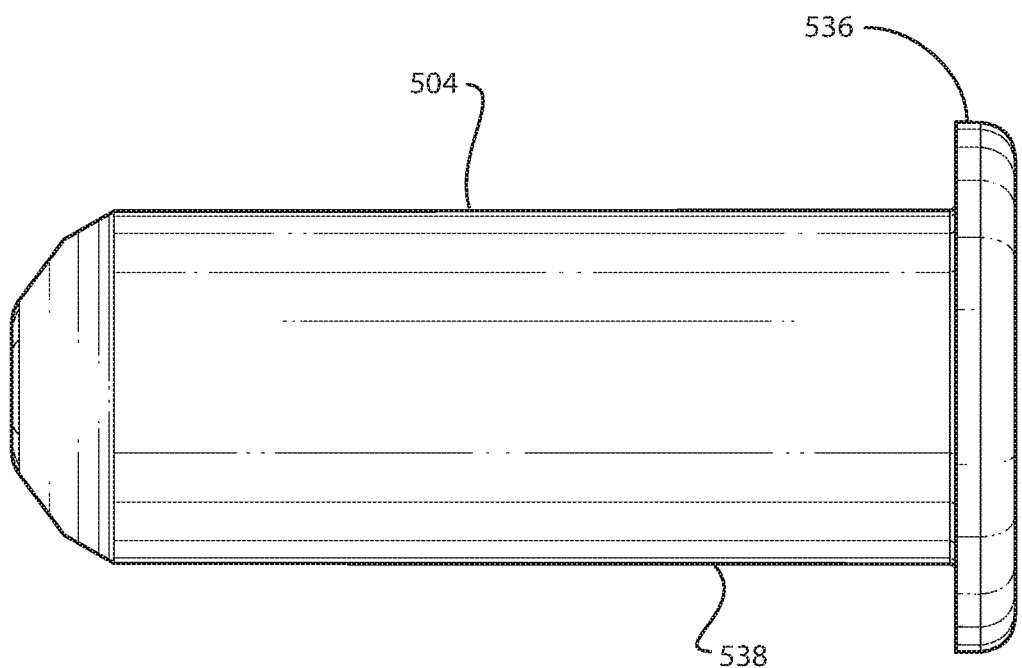
FIG. 8E is a top view of the implant of FIG. 8A.
Figure 8F:
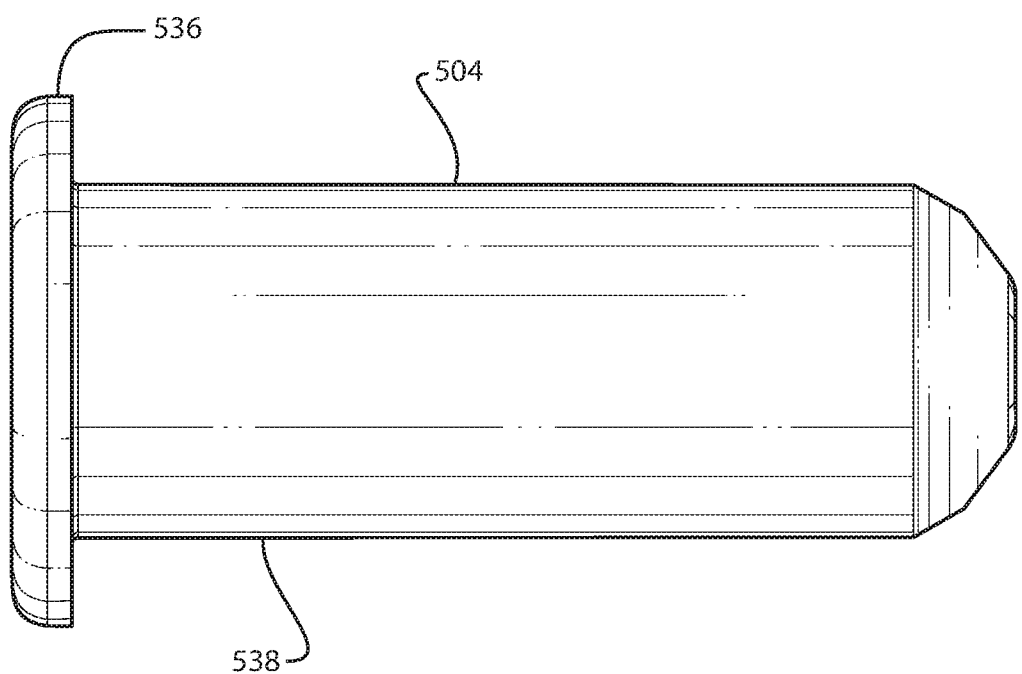
FIG. 8F is a bottom view of the implant of FIG. 8A.
Figure 8G:
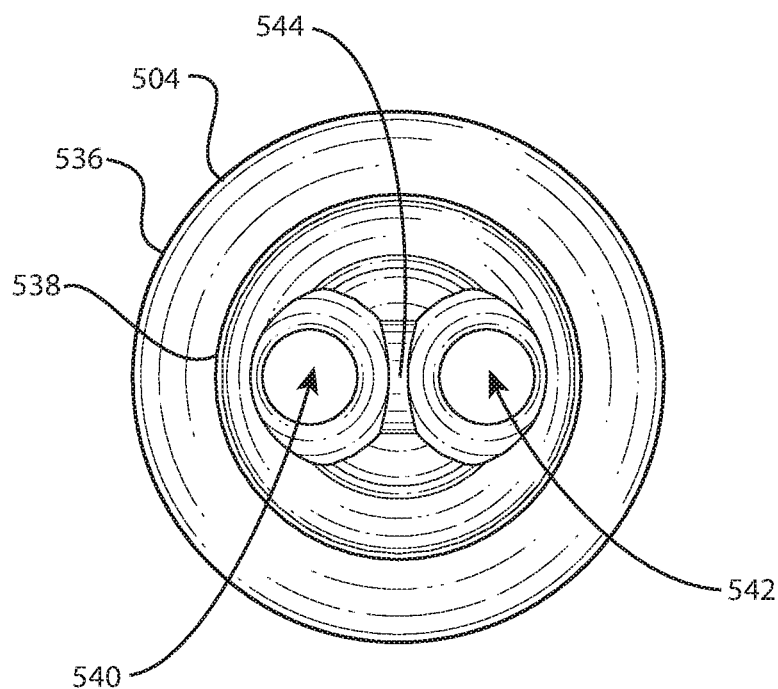
FIG. 8G is a left view of the implant of FIG. 8A.
Figure 8H:
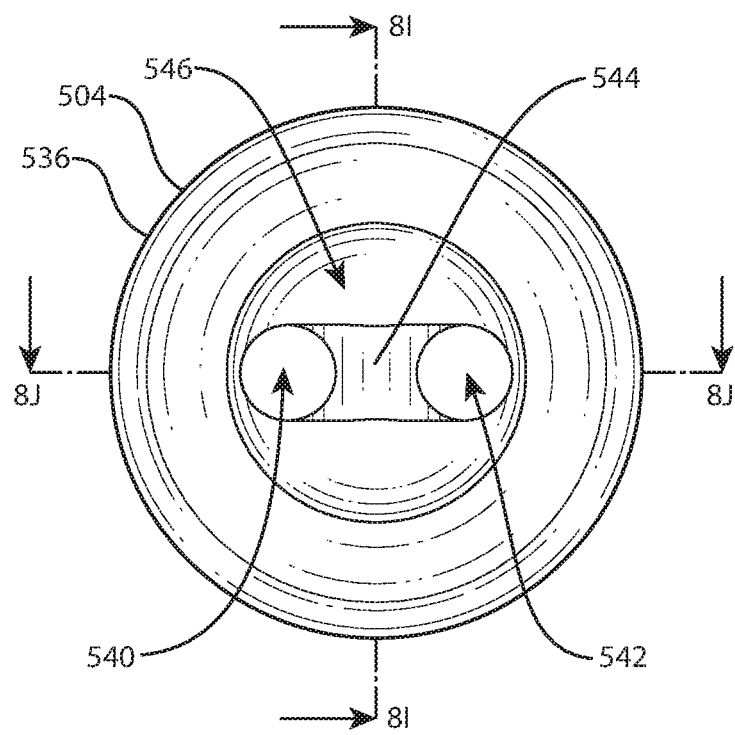
FIG. 8H is a right view of the implant of FIG. 8A.
Figure 8I:
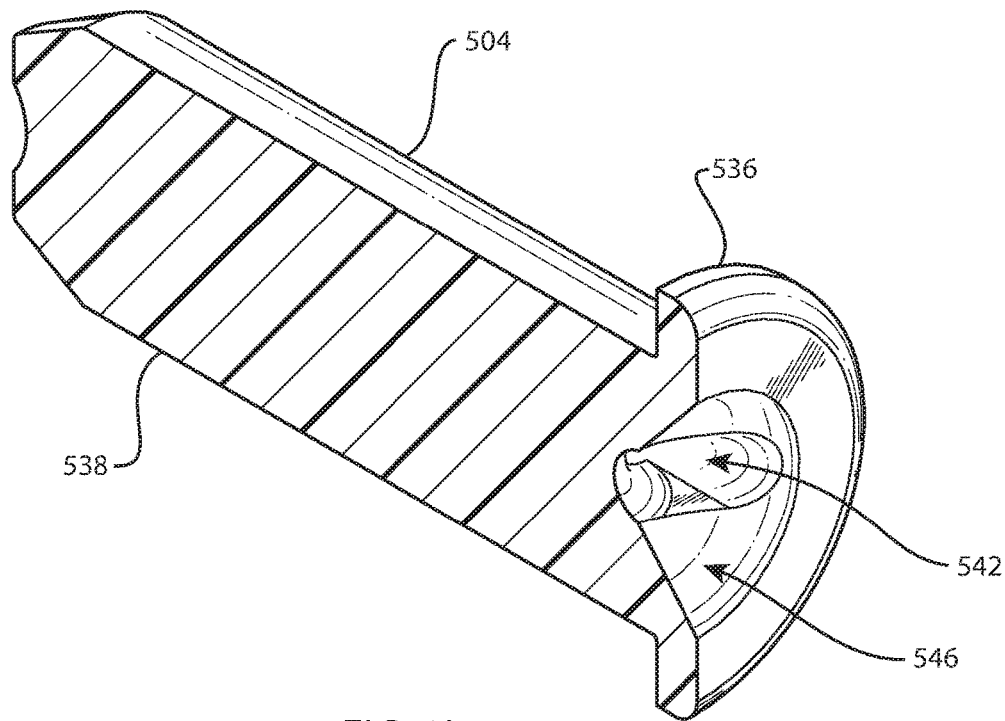
FIG. 8I is an isometric cross section view of the implant of FIG. 8H taken along section line 8I-8I of FIG. 8H.
Figure 8J:
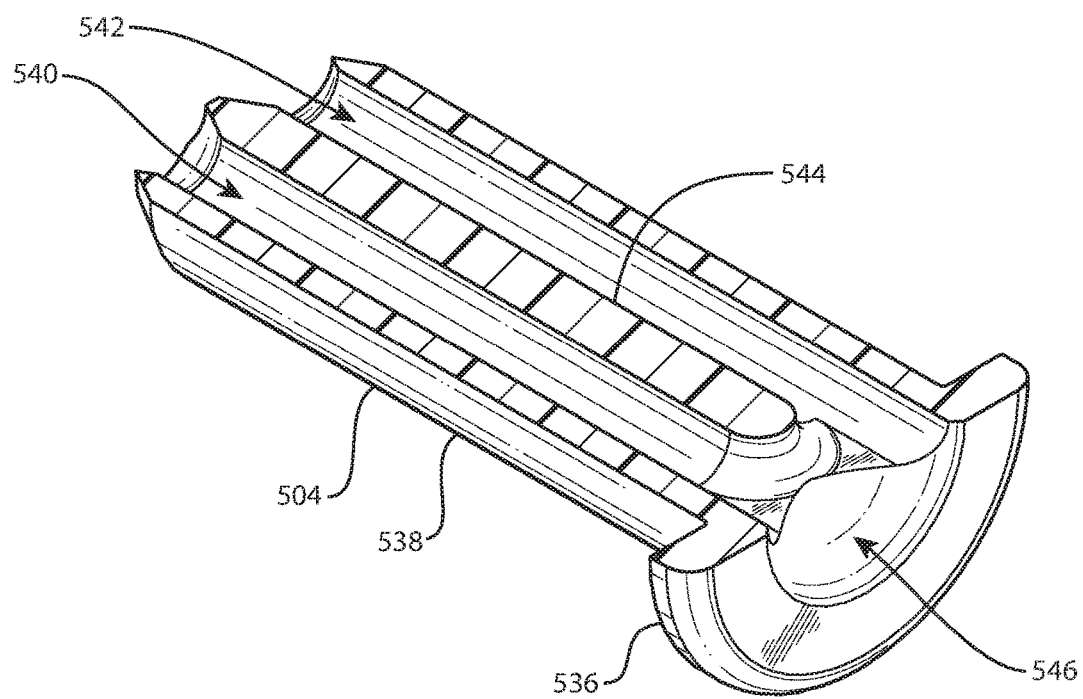
FIG. 8J is an isometric cross section view of the implant of FIG. 8H taken along section line 8J-8J of FIG. 8H.

Referring to FIGS. 4A-4C, the needle assembly 400 includes a flexible suture shuttle 402, a needle 404, and a handle 408. The needle assembly 400 may include an optional needle caddy 406. The needle assembly 400 may be referred to as a needle storage assembly 400 or a needle caddy assembly 400. The needle assembly 400 presents the needle 404, pre-loaded with the suture shuttle 402, for safe handling by surgical staff.

The suture shuttle 402 includes a loop 412 and a heel 414 at an opposite end of the suture shuttle 402 from the loop 412. At least the loop 412 may be fabricated from suture, cable, or other flexible filament. The heel 414 may be more substantial and less flexible than the loop 412, or the same as the loop 412.

The handle 408 includes a larger diameter portion 416 at one end of the handle 408 and a smaller diameter portion 418 at an opposite end of the handle 408. A longitudinal through hole 420 extends through the handle 408 and is sized to receive the heel 414 of the suture shuttle 402. The smaller diameter portion 418 may be fixed to the heel 414, for example by crimping, swaging, gluing, or ultrasonic welding. The suture shuttle 402 and the handle 408 together may be referred to as a needle threader 403.

The optional needle caddy 406 covers at least a portion of the needle 404 and supports the needle threader 403. The illustrated example is a rectangular block of foam or another resilient material. The needle caddy 406 includes a rectangular notch 422, a through hole 424 extending through the needle caddy 406 across the notch 422, and a slit 426 extending partially into the needle caddy from a side opposite the notch 422.

Referring to FIGS. 4B-5H, the needle 404 includes a point 428, a heel 430 at an end of the needle 404 opposite the point 428, and an eye 432 which extends transversely through the heel 430. The needle 404 tapers down to the point 428. The point 428 may be sharp or blunt.

The needle assembly 400 may be assembled by inserting the point 428 of the needle 404 in the slit 426 of the needle caddy 406, positioning the heel 430 of the needle in the notch 422 of the needle caddy, passing the suture shuttle 402 through the hole 424 of the needle caddy and the eye 432 of the needle so that the loop 412 and the heel 414 of the suture shuttle extend from opposite sides of the needle caddy 406, inserting the heel 414 into the hole 420 of the handle 408, and fixing the handle 408 to the heel 414. Optionally, the heel 414 may be inserted into the hole 420 of the handle 408 and the handle 408 may be fixed to the heel 414 before the suture shuttle 402 is passed through the hole 424 and the eye 432. Referring to FIG. 4A, the slit 426 of the needle caddy 406 receives and covers at least a portion of the needle 404 including the point 428. The notch 422 of the needle caddy 406 receives the heel 430 of the needle 404. The through hole 424 of the needle caddy 406 receives and supports the needle threader 403, which also passes through the eye 432 of the needle 404.

Referring to FIGS. 6A-6H, another needle 410 may substitute for the needle 404. The needle 410 includes a point 434, a heel 436 at an end of the needle 410 opposite the point 434, and an eye 438 which extends transversely through the heel 436. The needle 410 tapers down to the point 434. The point 434 may be sharp or blunt. The needle 410 includes a second eye 440 which extends transversely through the heel 436 adjacent to the first eye 438. In use, a first free end of a suture may be threaded through the first eye 438 and a second free end of the suture may be threaded through the second eye 440, creating a suture loop that follows the needle 410. The needle 410 and two free ends are passed through the plantar plate, the free ends are removed from the needle 410, and the free ends are passed through the suture loop to create a cinch stitch.

Referring to FIGS. 7A-7D, the implant assembly 500 includes an implant inserter 502, an implant 504, a first suture shuttle 506, and a second suture shuttle 508. The implant assembly 500 may be referred to as an implant inserter assembly 500. The implant assembly 500 presents the implant, pre-loaded with the first and second suture shuttles 506, 508, for efficient handling by surgical staff.

The implant inserter 502 is an elongated part with an implant engaging end 512 and a handle portion 514 at an opposite end of the implant inserter 502 from the implant engaging end 512. In this example, implant inserter 502 is a flat or plate-like part. A longitudinal hole 516 extends into the implant inserter 502 from the implant engaging end 512 and is sized to receive a portion of the first suture shuttle 506. The hole 516 may be sized to receive a portion of the first and second suture shuttles 506, 508. The hole 516 may be a blind hole, as shown, or a through hole. There may be a second hole (not shown) beside the hole 516 in an arrangement like that described below for the cannulations 540, 542 of the implant 504. In this arrangement, the hole 516 receives a portion of the first suture shuttle 506 and the second hole receives a portion of the second suture shuttle 508. The implant inserter 502 may include one or more features to retain portions of the first and second suture shuttles 506, 508, such as the illustrated bilateral slits 518, 520. The slit 518 may be sized so that the first suture shuttle 506 may be wedged into the slit 518. The slit 520 may be sized so that the second suture shuttle 508 may be wedged into the slit 520.

Figure 21A:
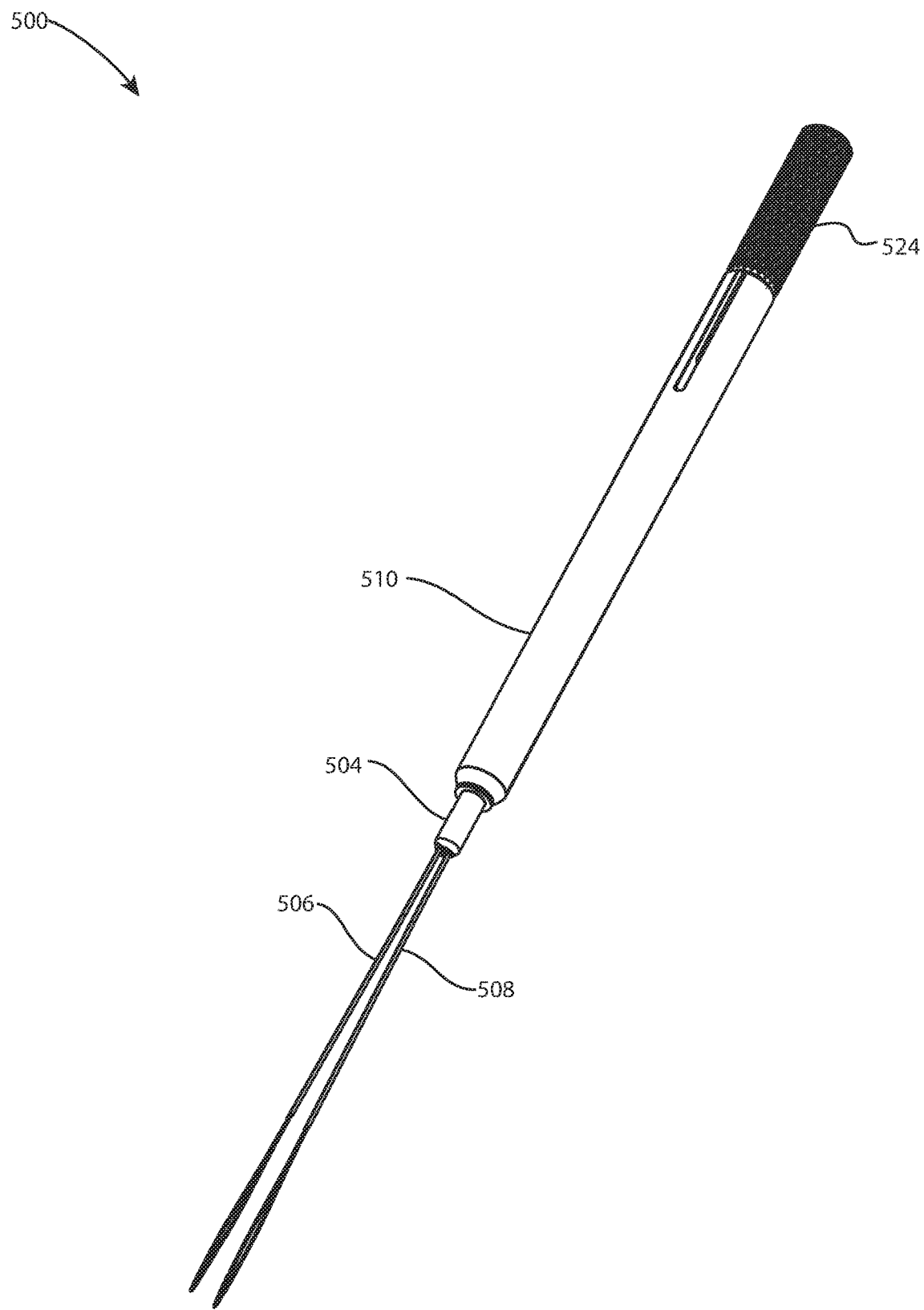
FIG. 21A is an isometric view of the implant assembly of FIG. 7A with a different implant inserter and a handle.
Figures 21B, 21C:
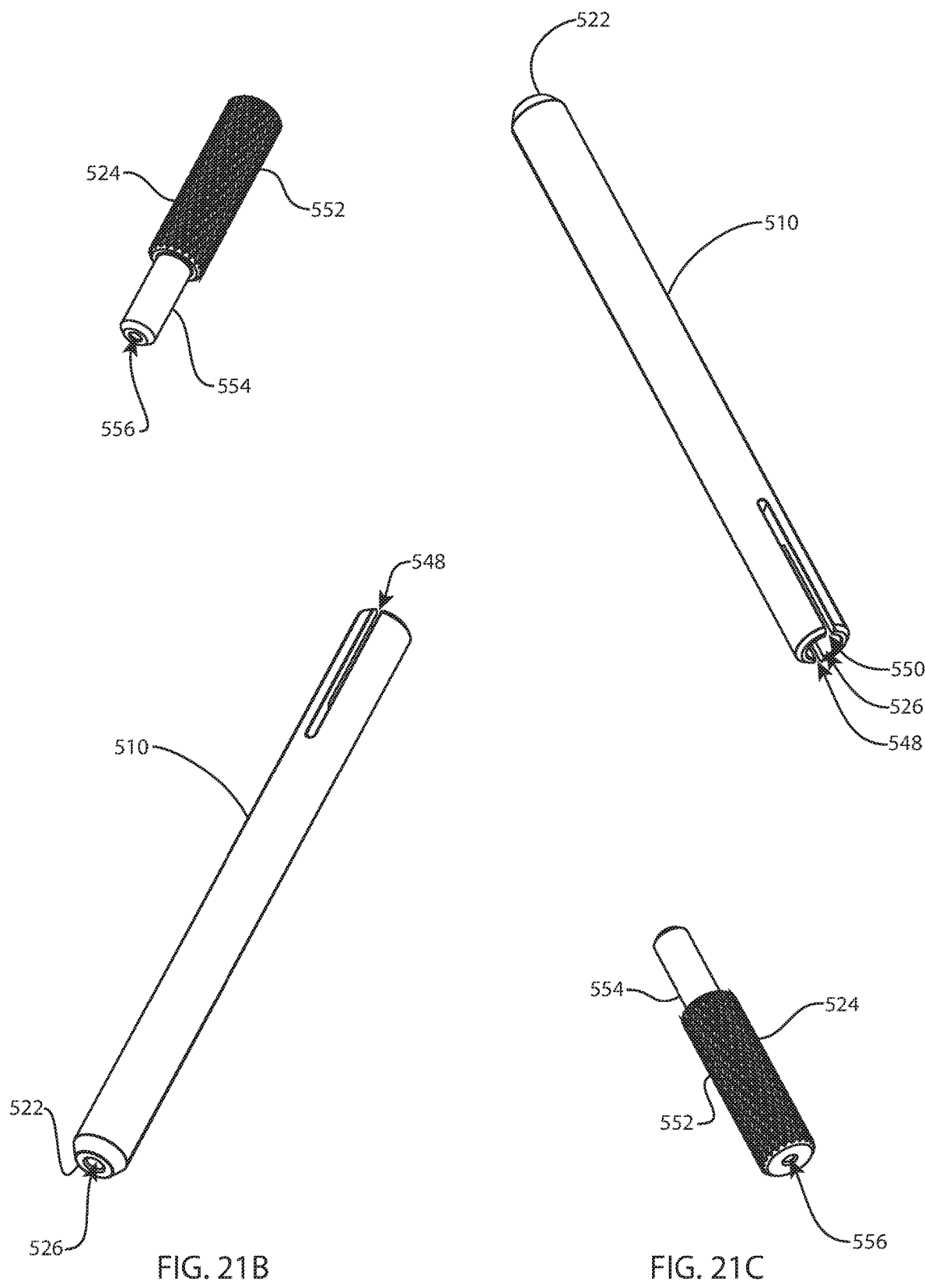
FIG. 21B is an exploded isometric view of the implant inserter and handle of FIG. 21A.
FIG. 21C is another exploded isometric view of the implant inserter and handle of FIG. 21A from a different viewpoint.

Referring to FIGS. 15-17 and 21A-21C, another implant inserter 510 may substitute for the implant inserter 502. FIG. 21A illustrates the implant assembly 500 with the implant inserter 510 and a handle 524. The implant inserter 510 is an elongated part with an implant engaging end 522. In the implant assembly 500, the handle 524 is at an opposite end of the implant inserter 510 from the implant engaging end 522. In this example, implant inserter 510 is a cylindrical part. A longitudinal hole 526 extends into the implant inserter 510 from the implant engaging end 522 and is sized to receive a portion of the first suture shuttle 506. The hole 526 may be sized to receive a portion of the first and second suture shuttles 506, 508. The hole 526 may be a blind hole or a through hole as shown. There may be a second hole (not shown) beside the hole 526 in an arrangement like that described below for the cannulations 540, 542 of the implant 504. In this arrangement, the hole 526 receives a portion of the first suture shuttle 506 and the second hole receives a portion of the second suture shuttle 508. The implant inserter 510 may include one or more features to retain portions of the first and second suture shuttles 506, 508. The implant inserter 510 includes bilateral slits 548, 550. The slits 548, 550 may enable the implant inserter 510 to resiliently grip the handle 524.

The handle 524 may be fixed to one or both of the heels 530, 534 of the first and second suture shuttles 506, 508 in the manner described above for the handle 408 and the suture shuttle 402 of the needle assembly 400. The handle 524 includes a larger diameter portion 552 at one end of the handle 524 and a smaller diameter portion 554 at an opposite end of the handle 524. A longitudinal through hole 556 extends through the handle 524 and is sized to receive one or both of the heels 530, 534 of the first and second suture shuttles 506, 508. The smaller diameter portion 554 may be fixed to one or both of the heels 530, 534, for example by crimping, swaging, gluing, or ultrasonic welding.

Referring to FIGS. 7B, 7C, and 8A-8J, the implant 504 includes a head 536 and a shaft 538 extending from the head 536. The head 536 has a larger outer diameter than the shaft 538, and may be described as a flange 536. The implant 504 includes side by side first and second cannulations 540, 542 which are separated by a septum 544. The cannulations 540, 542 extend through the implant 504. The septum 544 may be full length as shown or partial length. The implant 504 may include an optional depression 546 or concavity in the head 536 around the cannulations 540, 542. In use, the head 536 rests against the dorsal surface of the proximal phalanx and the shaft 538 extends toward the plantar surface of the foot.

The first suture shuttle 506 includes a loop 528 and a heel 530 at an opposite end of the suture shuttle 506 from the loop 528. At least the loop 528 may be fabricated from suture, cable, or other flexible filament. The heel 530 may be more substantial and less flexible than the loop 528, or the same as the loop 528.

The second suture shuttle 508 includes a loop 532 and a heel 534 at an opposite end of the suture shuttle 508 from the loop 532. At least the loop 532 may be fabricated from suture, cable, or other flexible filament. The heel 534 may be more substantial and less flexible than the loop 532, or the same as the loop 532. The second suture shuttle 508 is preferably identical to the first suture shuttle 506. The suture shuttles 402, 506, 508 may all be identical.

The implant assembly 500 may be assembled by passing the first suture shuttle 506 through the first cannulation 540 of the implant 504 and optionally through the hole 516 of the implant inserter 502 so that the loop 528 of the first suture shuttle 506 extends from a plantar end of the implant 504, passing the second suture shuttle 508 through the second cannulation 542 of the implant and optionally through the hole 516 of the implant inserter 502 so that the loop 532 of the second suture shuttle 508 extends from the plantar end of the implant 504, engaging the head 536 of the implant 504 with the implant engaging end 512 of the implant inserter 502, wedging the first suture shuttle 506 in the first slit 518 of the implant inserter 502, and wedging the second suture shuttle 508 in the second slit 520 of the implant inserter 502. The engagement between the head 536 of the implant 504 and the implant engaging end 512 of the implant inserter 502 may be as simple as abutting surfaces, or complementary engagement features may be provided on the head 536 and the implant engaging end 512. The implant 504 may be retained on the implant inserter 502 by the first and second suture shuttles 506, 508 wedged in the slits 518, 520.

Referring to FIG. 1, the packaging tray 108 includes various pockets or wells to organize and protect the contents of the kit 100. The example tray 108 shown in FIG. 1 includes a pocket 110 for the first and second k-wires 102, 104, a pocket 112 for the needle driver 200, a pocket 114 for the implant assembly 500, a pocket 116 for the third k-wire 106, a pocket 118 for the distractor 300, and a pocket 120 for the needle assembly 400. The pockets may be more or less form-fitting due to the individual characteristics of the contents, such as mass and/or fragility.

Figure 9:
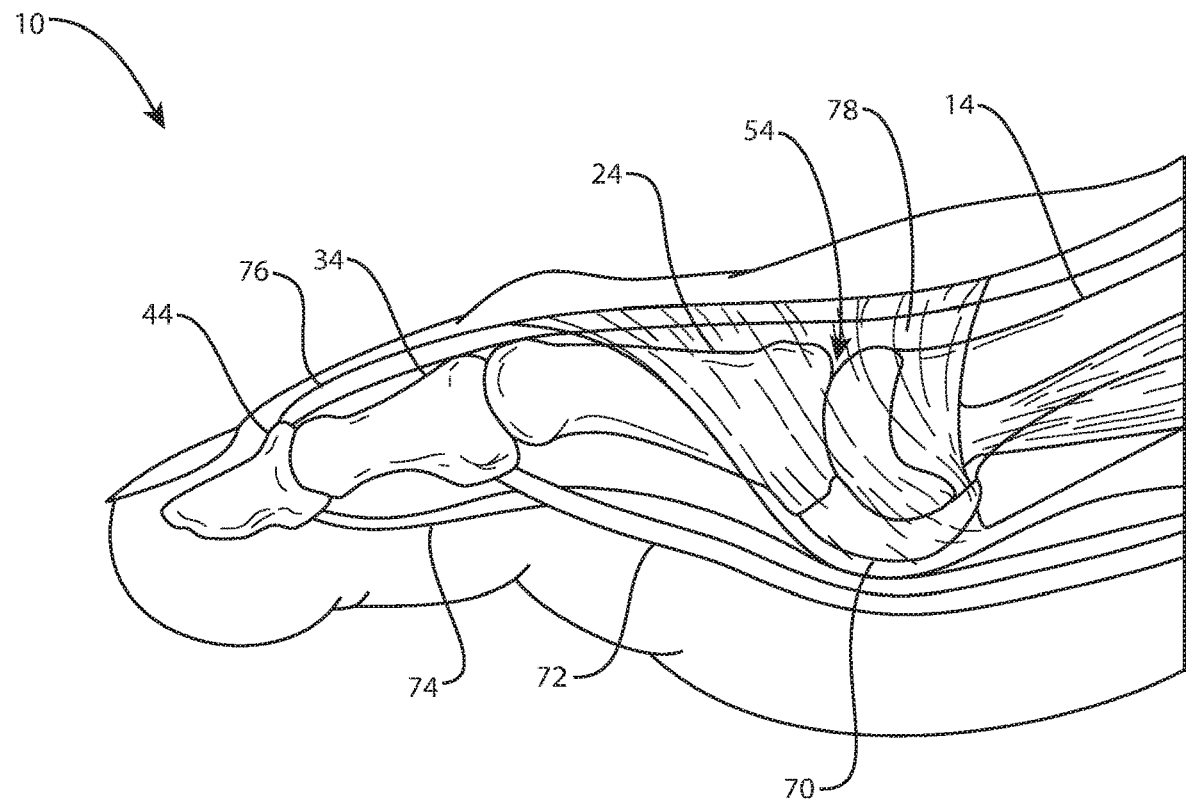
FIG. 9 is a lateral view of a second digit of a human foot illustrating selected internal structures.

Referring to FIG. 9, a normal human foot includes many soft tissue structures, including a plantar plate 70, a flexor digitorum brevis 72, a flexor digitorum longus 74, an extensor digitorum longus 76, and an extensor hood 78.

Figure 10:
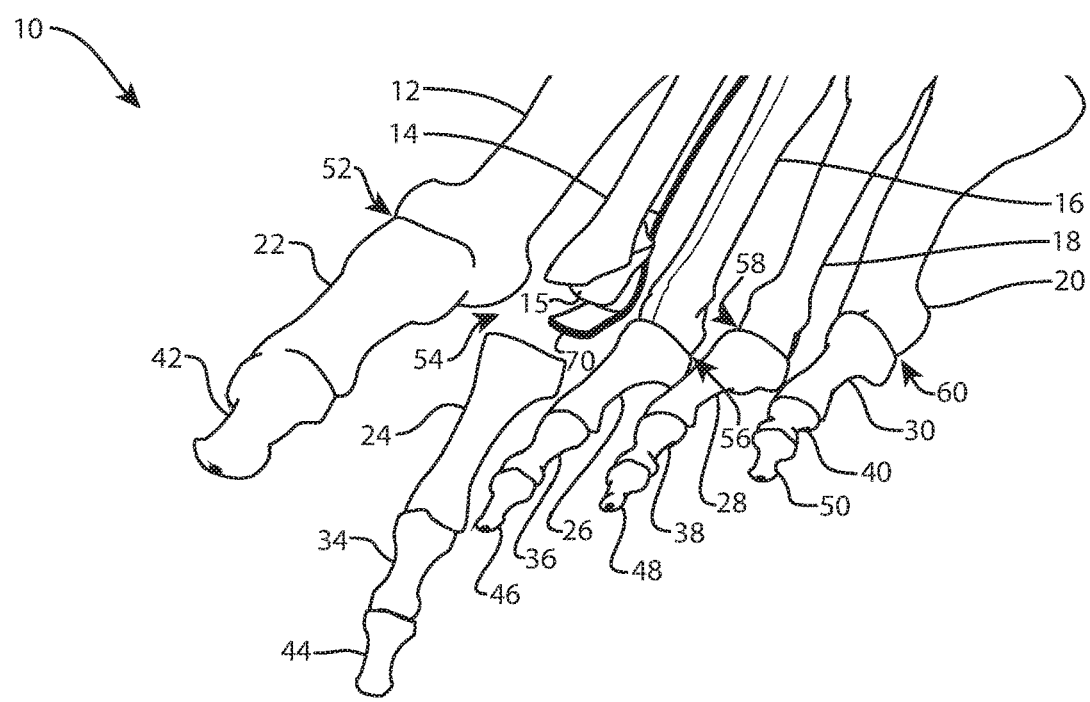
FIG. 10 is an isometric view of a second metatarsophalangeal joint after dissection and Weil osteotomy.

Referring to FIG. 10, a normal human foot 10 includes twenty-six bones, including a first metatarsal 12, a second metatarsal 14, a third metatarsal 16, a fourth metatarsal 18, a fifth metatarsal 20, a first proximal phalanx 22, a second proximal phalanx 24, a third proximal phalanx 26, a fourth proximal phalanx 28, a fifth proximal phalanx 30, a first middle phalanx 34, a second middle phalanx 36, a third middle phalanx 38, a fourth middle phalanx 40, a first distal phalanx 42, a second distal phalanx 44, a third distal phalanx 46, a fourth distal phalanx 48, and a fifth distal phalanx 50. The first metatarsal 12 and the first proximal phalanx 22 form a first metatarsophalangeal joint 52. The second metatarsal 14 and the second proximal phalanx 24 form a second metatarsophalangeal joint 54. The third metatarsal 16 and the third proximal phalanx 26 form a third metatarsophalangeal joint 56. The fourth metatarsal 18 and the fourth proximal phalanx 28 form a fourth metatarsophalangeal joint 58. The fifth metatarsal 20 and the fifth proximal phalanx 30 form a fifth metatarsophalangeal joint 60. A metatarsophalangeal joint may be referred to as an MTP joint.

Referring to FIGS. 9 and 10, the plantar plate 70 is a thick ligamentous structure on the bottom of the foot under a MTP joint. The plantar plate 70 attaches to a metatarsal and a corresponding proximal phalanx. The plantar plate 70 cushions the bottom of the MTP joint and the distal head of the metatarsal while standing, walking, running, and the like. The plantar plate 70 helps bring the toe to the floor while standing. FIG. 9 illustrates the plantar plate 70 associated with the second MTP joint 54. Each MTP joint 52, 54, 56, 58, 60 includes a plantar plate 70, although the plantar plates associated with the MTP joints 52, 56, 58, 60 are not illustrated for clarity.

Methods of plantar plate repair using the kit 100 will now be described.

Referring to FIG. 10, the second MTP joint 54 is exposed by creating a surgical incision that includes the second MTP joint 54, the plantar plate 70, and the flexors 72, 74. The plantar plate 70 is reflected, or detached, from the second proximal phalanx 24 and the flexor tendons 72, 74 (not shown for clarity). Optionally, a Weil osteotomy of the distal epiphysis of the second metatarsal 14 is performed, releasing a distal capital fragment 15 of the second metatarsal 14. The distal capital fragment 15 may be moved proximally as shown to provide greater exposure for the plantar plate repair procedure.

Figure 11:
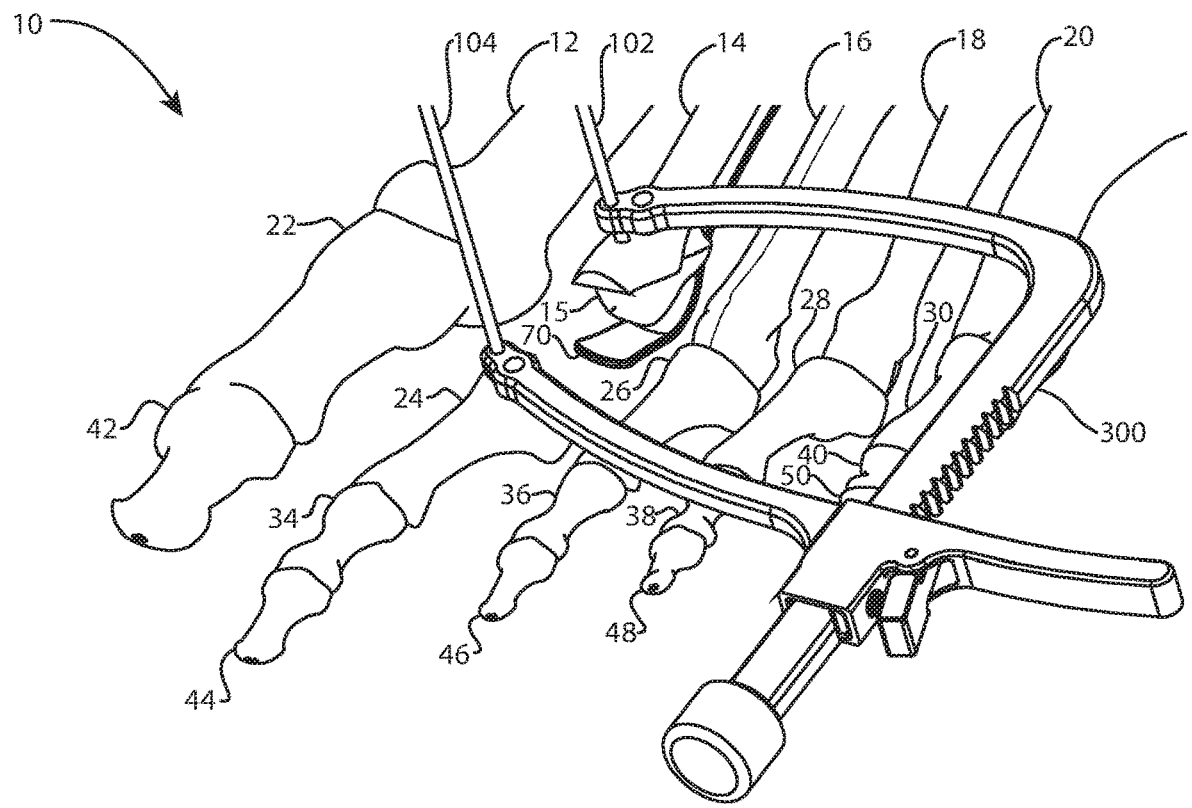
FIG. 11 is an isometric view of the second metatarsophalangeal joint of FIG. 10 after inserting k-wires and applying a distractor.

Referring to FIG. 11, the first k-wire is inserted through the distal epiphysis of the second metatarsal 14. If the optional Weil osteotomy was performed, the distal capital fragment 15 is temporarily fixed to a plantar aspect of the distal epiphysis of the second metatarsal 14 by inserting the first k-wire 102 through the distal epiphysis of the second metatarsal 14 and into the distal capital fragment 15. Note that only a single hole is made in the second metatarsal 14 to avoid weakening the second metatarsal 14 with additional holes, and to avoid taking the time necessary to prepare additional holes.

The second MTP joint 54 is distracted. This may be accomplished by inserting the second k-wire 104 through the proximal epiphysis of the second proximal phalanx 24, coupling the first arm 322 of the distractor 300 to the first k-wire 102 by passing the first k-wire 102 through the hole 324 of the first arm 322, coupling the second arm 340 of the distractor 300 to the second k-wire 104 by passing the second k-wire 104 through the hole 342 of the second arm 340, grasping the protrusion 328, and pushing on the cap 302 until adequate distraction is achieved. The third k-wire 106 may be used instead of the second k-wire 104, and may be passed through the hole 344 of the second arm 340. Note that only a single hole is made in the second proximal phalanx 24 to avoid weakening the second proximal phalanx 24 with additional holes, and to avoid taking the time necessary to prepare additional holes.

Figure 12:
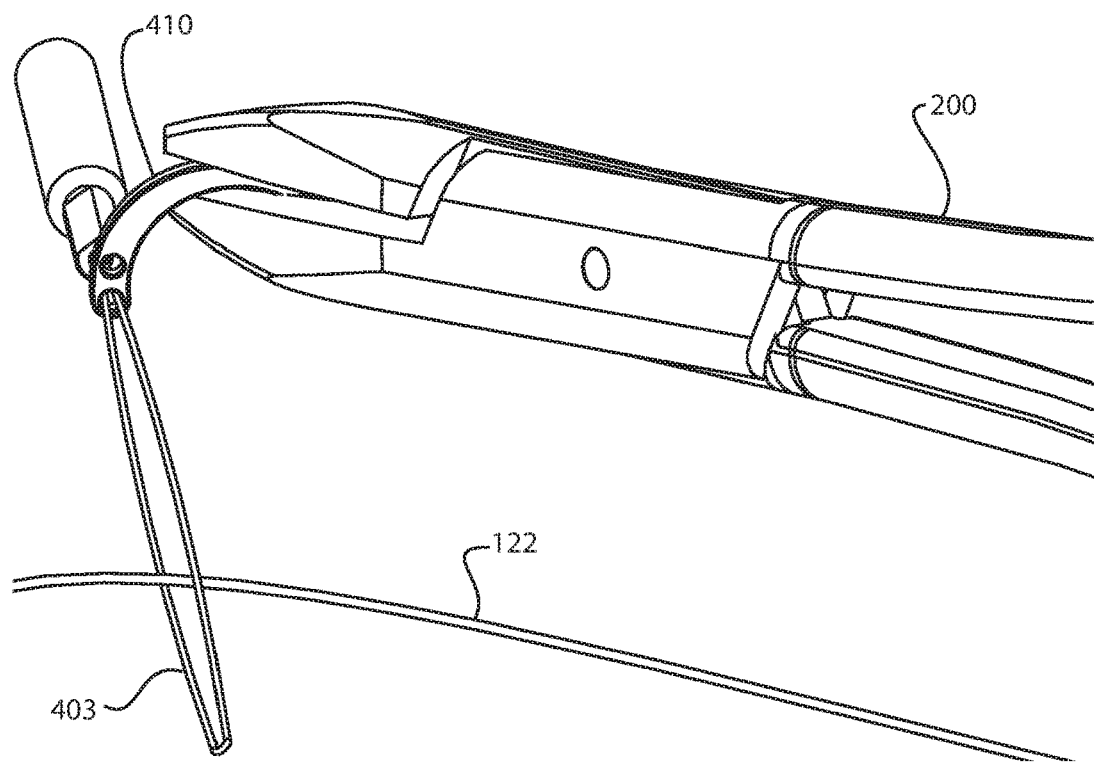
FIG. 12 is an isometric view of the needle driver of FIG. 2A, the needle of FIG. 6A, a needle threader of the needle assembly of FIG. 4A, and a suture.

Referring to FIG. 12, a suture 122 is threaded through the eye 438 of the needle 410 by passing a first free end of the suture 122 through the loop 412 of the needle threader 403 and pulling on the handle 408 of the needle threader to pull the suture 122 through the eye 438. This step may be performed while the needle 410 is held by the needle driver 200 as shown, or while the needle is assembled in the needle assembly 400 (FIG. 4A), with or without the optional needle caddy 406. The needle 410 with suture 122 through eye 438 may be removed from the optional needle caddy 406 with the needle driver 200.

Figure 13:
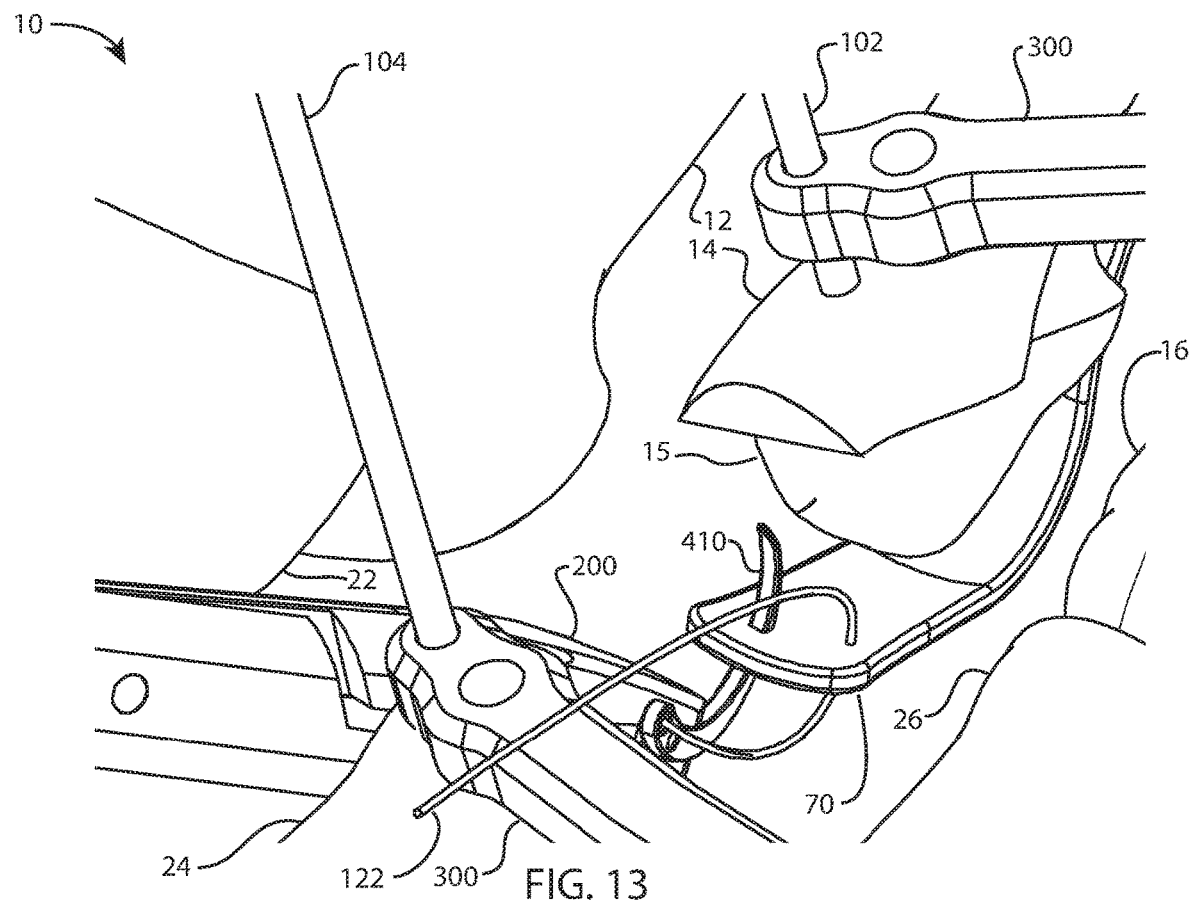
FIG. 13 is an isometric view of the second metatarsophalangeal joint of FIG. 11 after making a first stitch in a plantar plate of the joint and inserting the needle of FIG. 6A into the plantar plate for a second stitch.

Referring to FIG. 13, the suture 122 is passed through a distal portion of the plantar plate 70 to make one or more stitches. This may be accomplished by passing the suture 122 through the distal portion of the plantar plate 70 with the needle 410, grasping and manipulating the needle 410 with the needle driver 200. A first stitch is shown; a second stitch is in progress.

Figure 14:
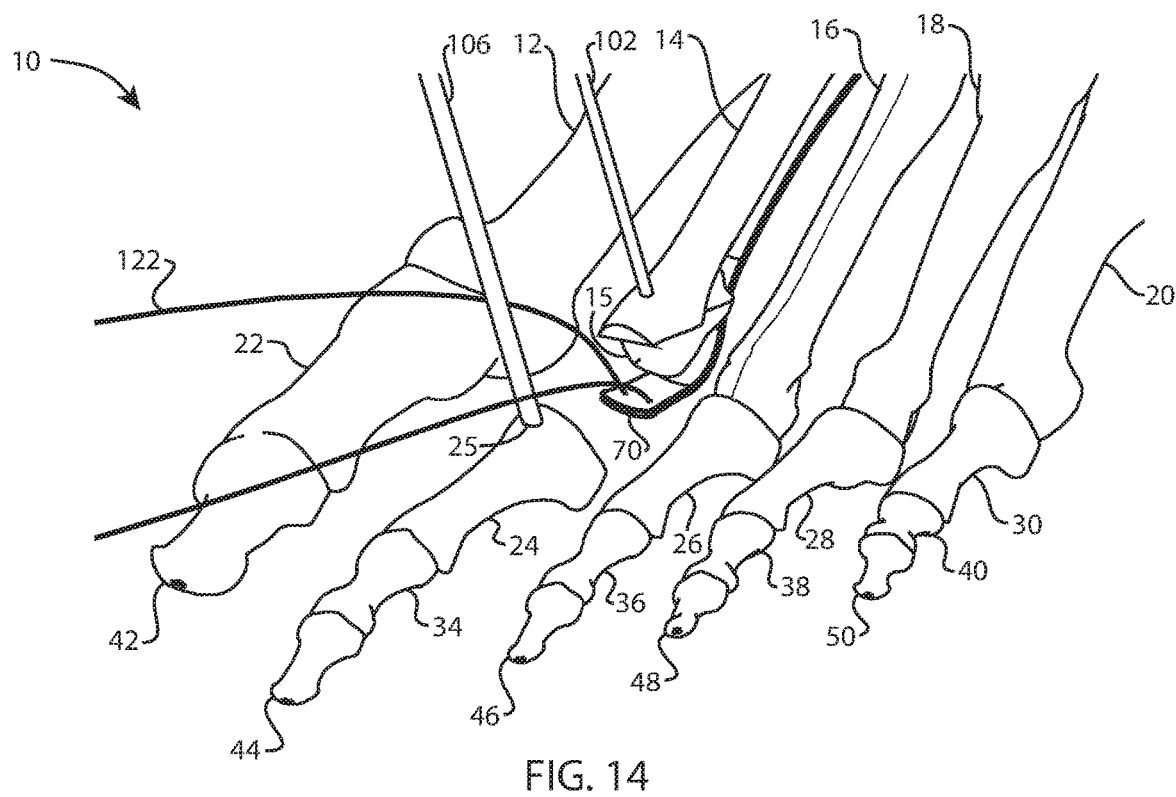
FIG. 14 is an isometric view of the second metatarsophalangeal joint of FIG. 13 after making the second stitch, removing the distractor, and replacing the distal k-wire with a Steinmann pin.

Referring to FIG. 14, two stitches have been made, together forming a mattress stitch. If the second k-wire 104 was used in the second proximal phalanx 24, a bone tunnel 25 may be formed through the proximal epiphysis of the second proximal phalanx 24 by removing the second k-wire 104 from the second proximal phalanx 24 leaving a hole through the second proximal phalanx 24, inserting the third k-wire 106 in the hole, and removing the third k-wire 106 from the second proximal phalanx 24 leaving the bone tunnel 25 through the second proximal phalanx 24. If the third k-wire 106 was used initially (FIG. 11), then remove the third k-wire 106 to leave the bone tunnel 25. Note that only a single hole/bone tunnel 25 is made in the second proximal phalanx 24 to avoid weakening the second proximal phalanx 24 with additional holes, and to avoid taking the time necessary to prepare additional holes.

Figure 15:
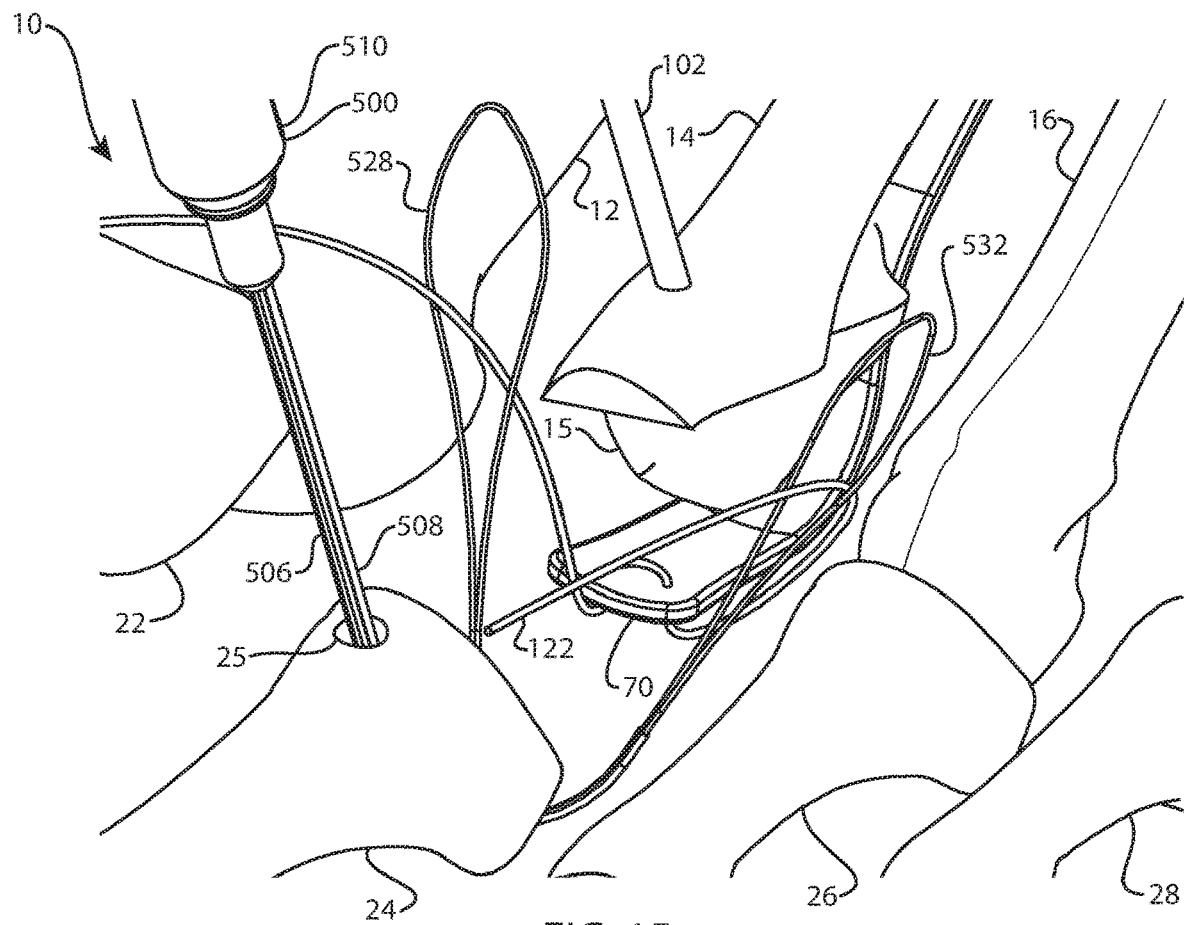
FIG. 15 is an isometric view of the second metatarsophalangeal joint of FIG. 14 after removing the Steinmann pin, passing suture retrieval loops through the resulting hole, and passing free ends of the suture through the suture retrieval loops.

Referring to FIG. 15, the first and second suture shuttles 506, 508 of the implant assembly 500 are passed through the bone tunnel 25 toward the plantar side of the foot. This can occur simultaneously or sequentially. The first free end of the suture 122 is passed through the loop 528 of the first suture shuttle 506 and a second free end of the suture 122 is passed through the loop 532 of the second suture shuttle 508. This can occur simultaneously or sequentially. Note that the first and second free ends of the suture 122 are passed through the loops 528, 532, respectively, outside of the confines of the second MTP joint 54 so that there is plenty of room in which to manipulate the free ends and/or loops. The first and second free ends of the suture 122 may be passed through the loops 528, 532, respectively, outside of the patient's foot, in other words, exterior to the patient's skin. Note that FIG. 15 illustrates the implant inserter 510 in the implant assembly 500 and shows a reverse mattress stitch compared to FIGS. 14.

Figure 16:
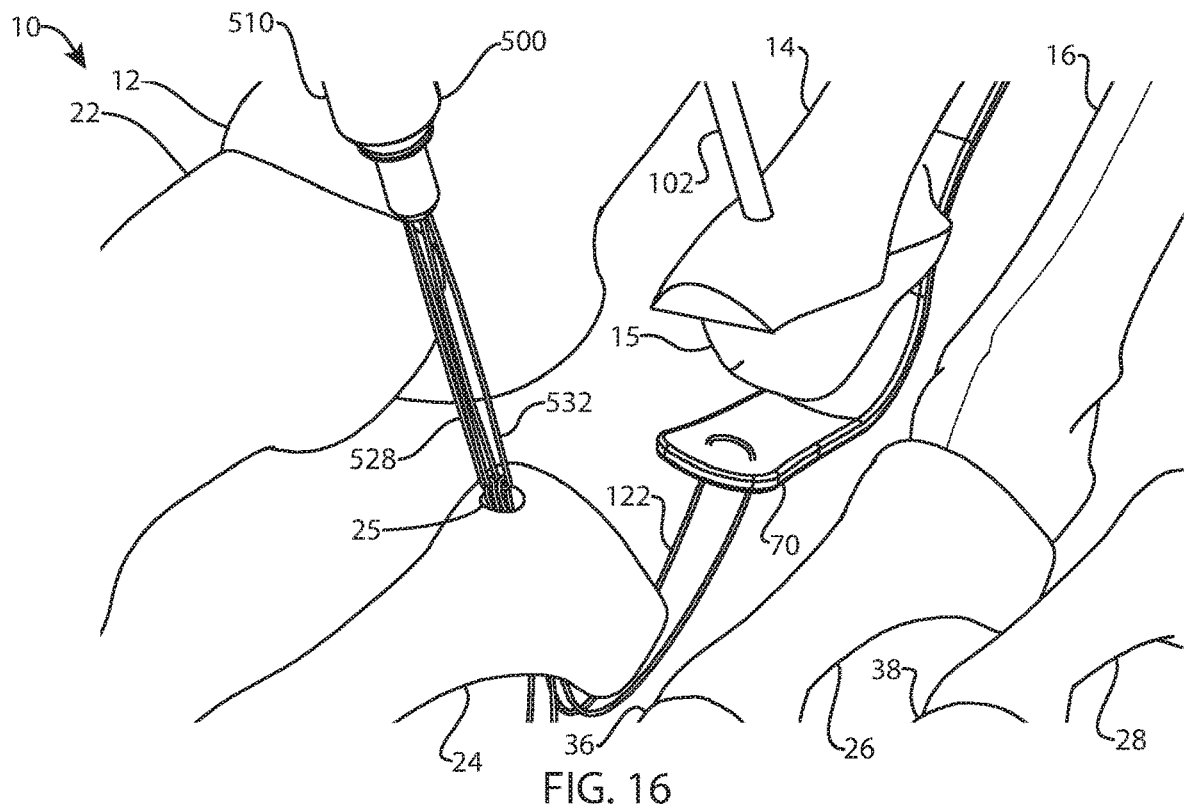
FIG. 16 is an isometric view of the second metatarsophalangeal joint of FIG. 15 after pulling on the suture retrieval loops to pass the suture through the hole.

Referring to FIG. 16, the first free end of the suture 122 is passed in a dorsal direction through the bone tunnel 25, the first cannulation 540 of the implant 504, and optionally the first longitudinal hole of the implant inserter 510 by pulling on the heel 530 of the first suture shuttle 506. The second free end of the suture 122 is passed in a dorsal direction through the bone tunnel 25, the second cannulation 542 and optionally the first longitudinal hole of the implant inserter 510 by pulling on the heel 534 of the second suture shuttle 508. The heels 530, 534 may be pulled simultaneously or sequentially.

Figure 17:
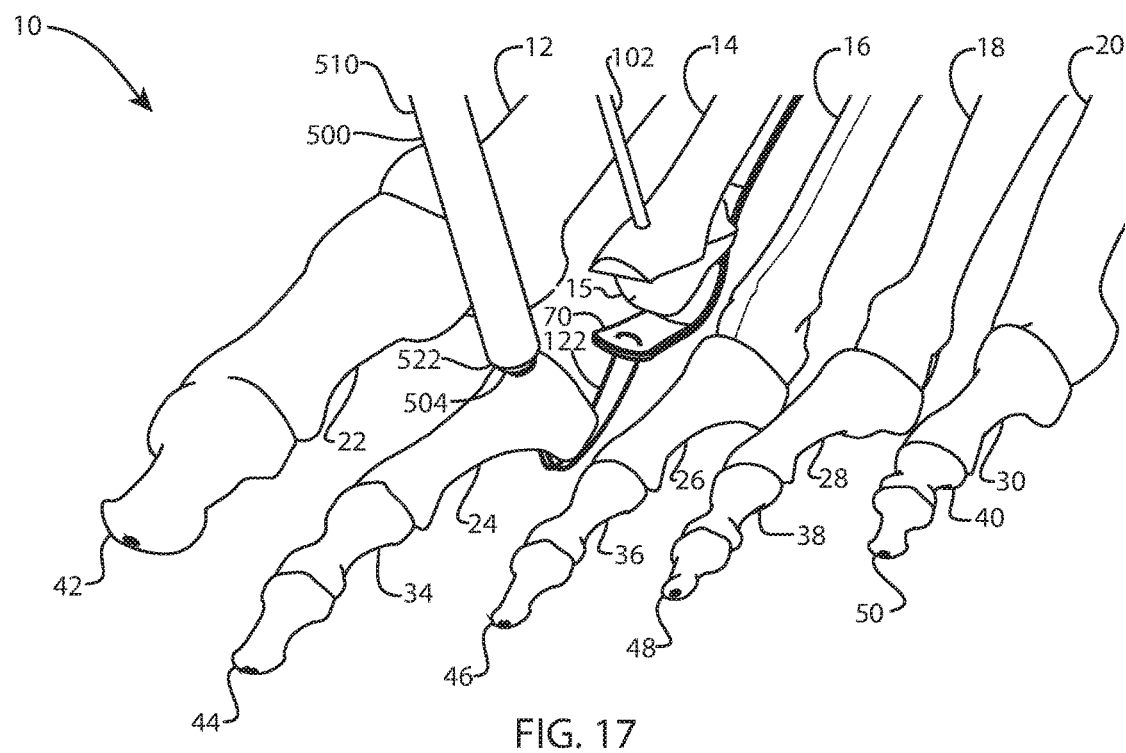
FIG. 17 is an isometric view of the second metatarsophalangeal joint of FIG. 16 after advancing the implant of FIG. 8A into the hole.

Referring to FIG. 17, the plantar end of the implant 504 is advanced into the bone tunnel 25 until the head 536 of the implant 504 rests against the dorsal aspect of the second proximal phalanx 24. The implant inserter 510 may be used to push the implant 504 into the bone tunnel 25.

Figure 18:
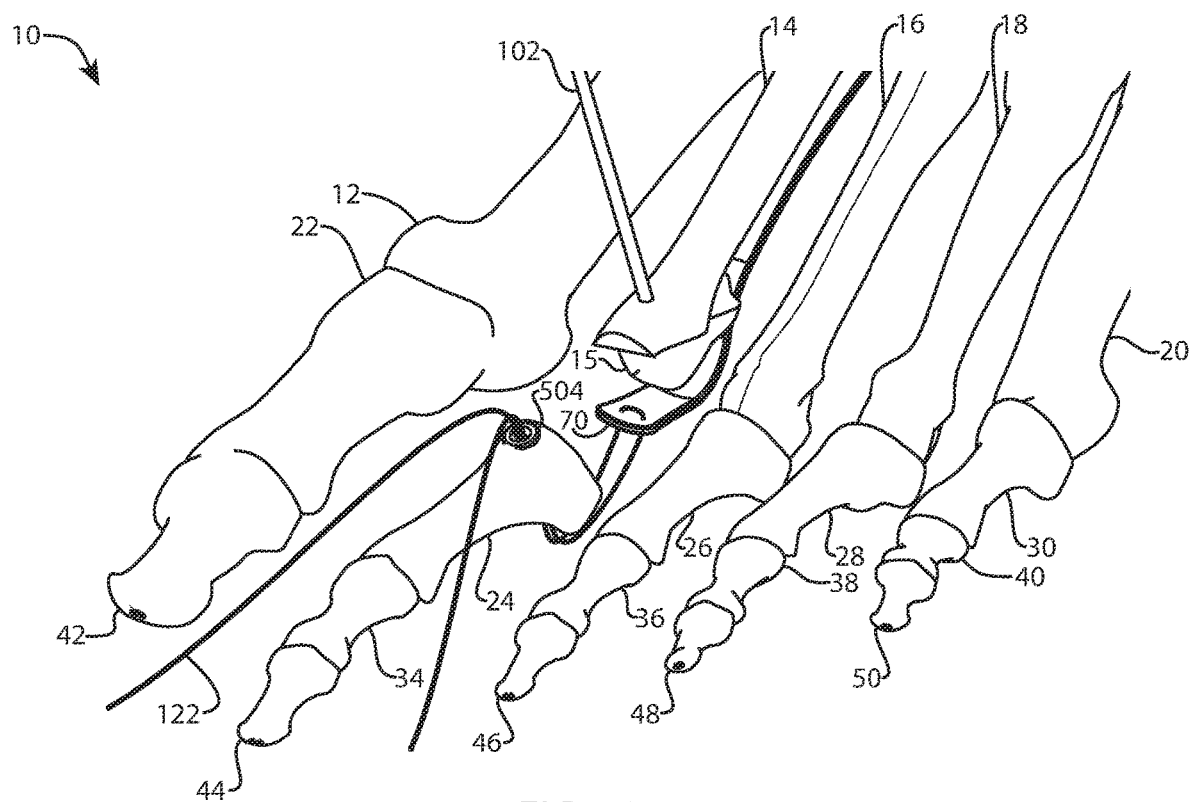
FIG. 18 is an isometric view of the second metatarsophalangeal joint of FIG. 17 after removing an inserter of the implant assembly of FIG. 7A.

Referring to FIG. 18, the implant inserter is decoupled from the dorsal end of the implant 504.

Figure 19:
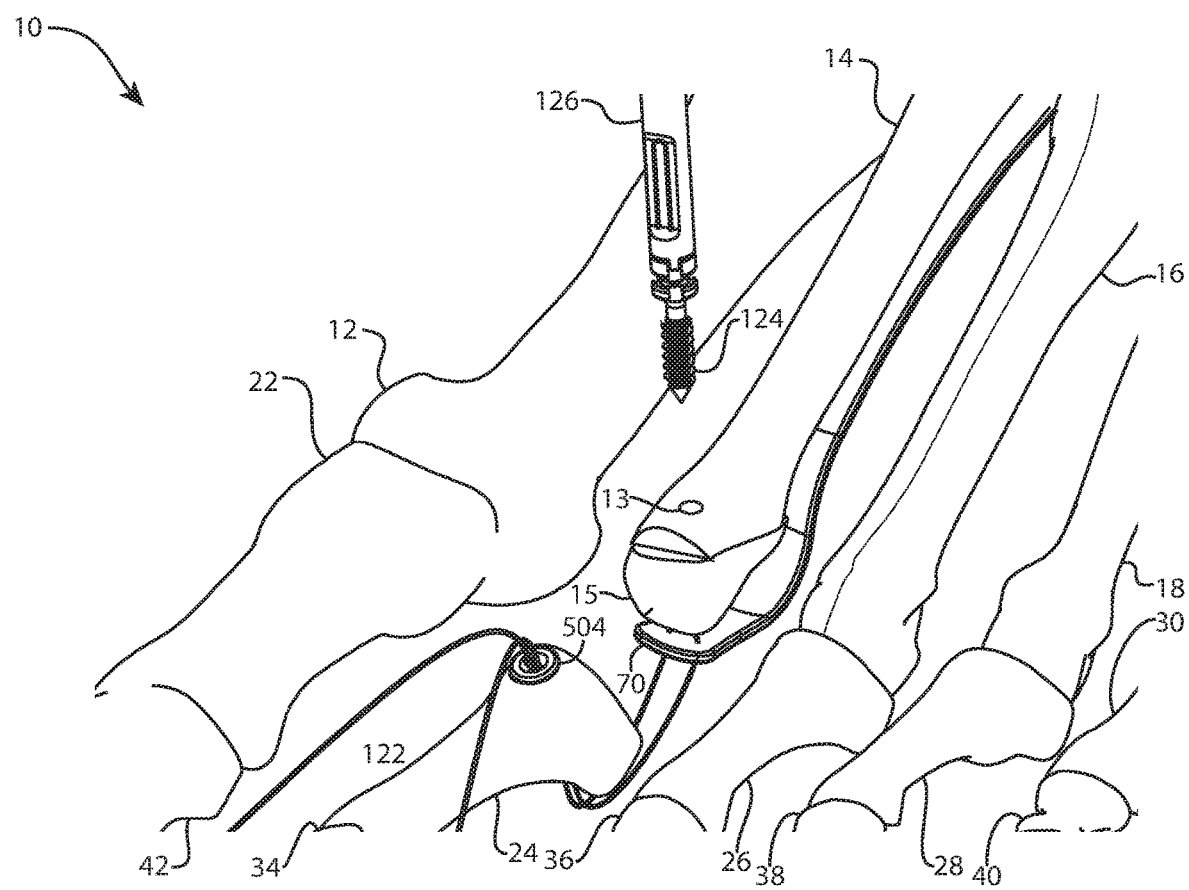
FIG. 19 is an isometric view of the second metatarsophalangeal joint of FIG. 18 after reducing a distal capital fragment of the second metatarsal against the distal epiphysis of the second metatarsal.

Referring to FIG. 19, the first k-wire 102 is removed from the distal epiphysis of the second metatarsal 14, leaving a hole 13 through the distal epiphysis of the second metatarsal 14. If an optional Weil osteotomy was performed, the temporary fixation of the distal capital fragment 15 to the distal epiphysis of the second metatarsal 14 is removed. This may be accomplished by removing the first k-wire 102 from the distal epiphysis of the second metatarsal 14 and the distal capital fragment 15, leaving a hole 13 through the distal epiphysis of the second metatarsal 14 and the distal capital fragment 15. The distal capital fragment 15 is reduced against the distal epiphysis of the second metatarsal 14. FIG. 19 illustrates a bone screw 124, coupled to a screwdriver 126, in position to be driven into the hole 13. Note that the hole 13 made by the first k-wire 102 is used for the bone screw 124 so that only a single hole need be made in the second metatarsal 14.

Figure 20:
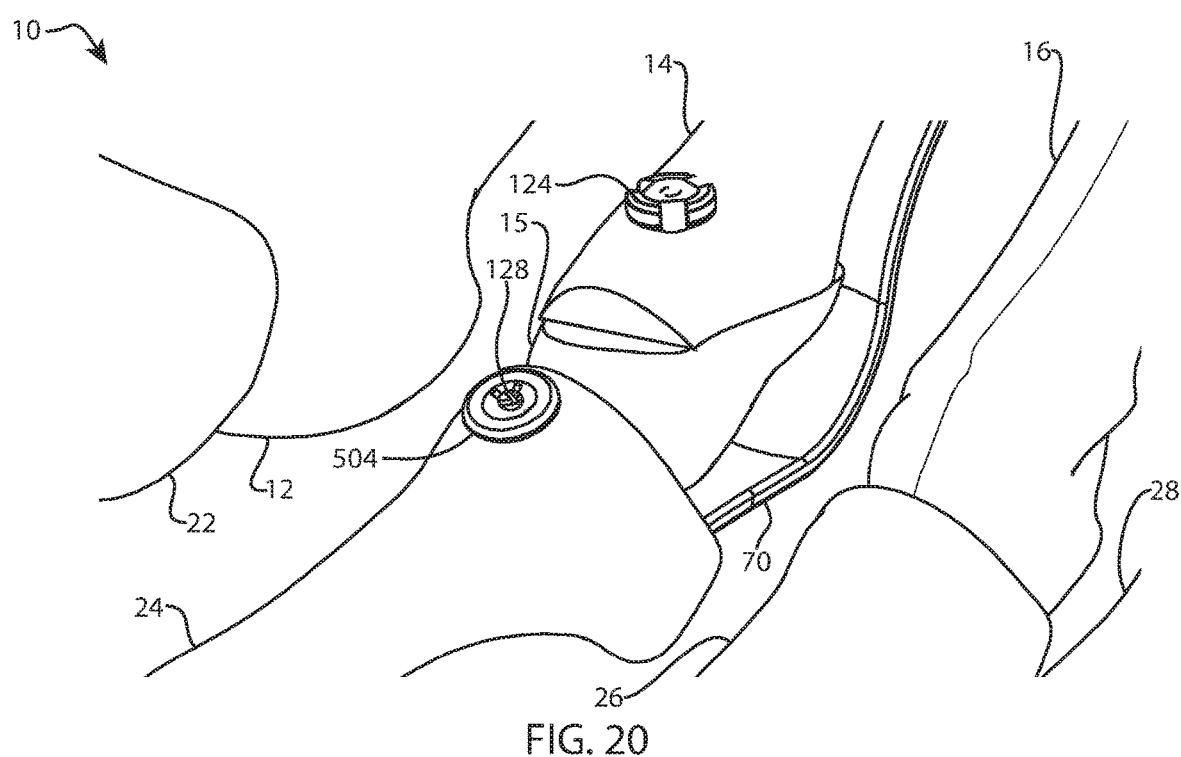
FIG. 20 is an isometric view of the second metatarsophalangeal joint of FIG. 19 after inserting a screw through the distal epiphysis and the distal capital fragment of the second metatarsal, tensioning the sutures, and tying a knot against the implant.

Referring to FIG. 20, the distal capital fragment 15, if present, is secured to the distal epiphysis of the second metatarsal 14 by the bone screw 124. The second proximal phalanx 24 is reduced relative to the second metatarsal 14. The suture 122 is tensioned and a knot 128 is tied over the septum 544 of the implant 504. The knot 128 rests in the depression 546 of the implant 504. The surgical incision is closed.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A method for plantar plate repair, comprising:
   exposing a metatarsophalangeal joint, wherein the metatarsophalangeal joint comprises a metatarsal, a proximal phalanx, and a plantar plate;
   providing a suture having a first free end and a second free end opposite the first free end;
   passing the suture through a distal portion of the plantar plate;
   passing the first and second free ends of the suture in a single motion through a proximal epiphysis of the proximal phalanx; and
   securing the first and second free ends of the suture together adjacent to the dorsal aspect of the proximal epiphysis of the proximal phalanx.

2. The method of claim 1, wherein passing the first and second free ends of the suture in a single motion comprises passing the first and second free ends of the suture simultaneously.

3. The method of claim 1, comprising:
   providing a first suture shuttle and a second suture shuttle;
   passing the first and second suture shuttles through the proximal epiphysis of the proximal phalanx;
   passing the first free end of the suture through the first suture shuttle;
   passing the second free end of the suture through the second suture shuttle;
   passing the first free end of the suture through the proximal epiphysis of the proximal phalanx by pulling a proximal end of the first suture shuttle;
   passing the second free end of the suture through the proximal epiphysis of the proximal phalanx by pulling a proximal end of the second suture shuttle;
   reducing the proximal phalanx relative to the metatarsal;
   tensioning the suture;
   tying the first and second free ends of the suture together with a knot, wherein the knot rests against the dorsal aspect of the proximal epiphysis of the proximal phalanx; and
   closing the exposure of the metatarsophalangeal joint.

4. The method of claim 3, wherein the proximal ends of the first and second suture shuttles are simultaneously pulled.

5. The method of claim 4, comprising:
   providing an assembly comprising the first and second suture shuttles and a handle, wherein the proximal ends of the first and second suture shuttles are coupled to the handle so that the second suture shuttle extends beside the first suture shuttle;
   wherein pulling on the handle pulls on the proximal ends of the first and second suture shuttles.

* * * * *